(12) United States Patent
Tsadik

(10) Patent No.: US 12,419,649 B2
(45) Date of Patent: Sep. 23, 2025

(54) COMPRESSION GARMENT FOR WINDING AND APPLYING ON LEG, ARM OR UPPER LIMB

(71) Applicant: TWM—TSADIK WIESER MEDICAL LTD, Otniel (IL)

(72) Inventor: Yaakov Tsadik, Jerusalem (IL)

(73) Assignee: TWM—TSADIK WIESER MEDICAL LTD, Otniel (IL)

( * ) Notice: Subject to any disclaimer, the term of this patent is extended or adjusted under 35 U.S.C. 154(b) by 0 days.

(21) Appl. No.: 19/058,548

(22) Filed: Feb. 20, 2025

(65) Prior Publication Data

US 2025/0186057 A1    Jun. 12, 2025

Related U.S. Application Data

(63) Continuation of application No. PCT/IL2024/050462, filed on May 13, 2024.

(60) Provisional application No. 63/563,801, filed on Mar. 11, 2024.

(51) Int. Cl.
*A61B 17/132* (2006.01)
*A61B 17/12* (2006.01)

(52) U.S. Cl.
CPC  *A61B 17/1322* (2013.01); *A61B 2017/12004* (2013.01)

(58) Field of Classification Search
CPC .............. A61B 17/132; A61B 17/1322; A61B 17/1325; A61B 2017/12004
See application file for complete search history.

(56) References Cited

U.S. PATENT DOCUMENTS

| | | |
|---|---|---|
| 2008/0177159 A1 | 7/2008 | Gavriely |
| 2012/0071917 A1 | 3/2012 | McDonald et al. |
| 2013/0267994 A1 | 10/2013 | Crowder et al. |
| 2022/0039805 A1 | 2/2022 | Hsiao |

OTHER PUBLICATIONS

International Search Report and Written Opinion dated Jul. 2, 2024 in PCT Application PCT/IL2024/050462.

*Primary Examiner* — Ryan J. Severson
(74) *Attorney, Agent, or Firm* — Pillsbury Winthrop Shaw Pittman LLP

(57) ABSTRACT

A compression garment for winding and applying a tension force that includes a belt including a first strip having two belt openings and a second strip being a smooth fabric, a buckle, a rod and a rod holder configured for holding said rod. The second strip is threaded into said rod, folded in half and enters said first strip along with said rod. A compression unit can include a cone, a cone bolt, a bolt disk, a cone holder having a cone holder opening for said cone bolt attaching said cone to said cone holder, and a bridge configured on upper side of said belt openings. The cone can have a cone opening through which said cone bolt may enter and be screwed with said bolt disk to said cone holder. The cone can be moveable on said bridge, and is configured detached from said cone holder.

20 Claims, 30 Drawing Sheets

Step 5

COMPRESSION GARMENT FOR WINDING AND APPLYING ON LEG, ARM OR UPPER LIMB

FIELD OF THE DISCLOSURE

The present disclosure, in some embodiments thereof, relates to devices for temporarily constricting or obstructing an artery supplying blood to one or more bodily parts, to control bleeding therefrom, and more particularly, but not exclusively, to a compression garment for temporarily constricting or obstructing an artery to the leg, arm or upper limb (neck, shoulder, upper thigh), to control bleeding therefrom, and applications thereof. Some embodiments of the disclosure are applicable for facilitating temporary arterial obstruction in bodily junctional areas, to control blood flowing therefrom.

BACKGROUND OF THE DISCLOSURE

Compression garments, such as tourniquets, are instruments or devices employed for temporarily constricting or obstructing an artery for the limb area, to control, and hopefully, stop, bleeding therefrom, so as to prevent death of a wounded person (or animal) due to large loss of blood. Constriction or obstruction is done externally (i.e., from outside the body), so as to reach and apply pressure to an artery of, or connected to, a bleeding wound.

Historically, the three main types of such garments are: the Dutch tourniquet, the Russian tourniquet, and the rubber tourniquet. The Dutch tourniquet is the simplest, consisting of a bandage or piece of cloth tightly applied and wrapped around a bleeding wound. The Russian tourniquet consists of a bandage or piece of cloth, along with a stick or piece of wood, tightly applied and wrapped around a bleeding wound. The rubber tourniquet consists of a rubber or rubber-like band tightly applied and wrapped around an entire limb having a bleeding wound.

More recently developed and used are the 'combat application tourniquet' (CAT), and junctional type tourniquets. The combat application tourniquet consists of a strong band and a pulley type mechanism for tightly applying and wrapping the band around a bleeding wound or immediate region thereof. Junctional type tourniquets consist of different types of materials and mechanisms for applying pressure, not directly to an artery of a bleeding wound, rather, to a (junction or connection) point (i.e., a pressure point) or region along the body (and circulatory system thereof) joining, connecting, or leading to the artery of the bleeding wound. Junctional type tourniquets are particularly useful for controlling and stopping bleeding in a wounded person having an amputated leg or an injury to an upper extremity (shoulder, or arm areas).

Exemplary teachings about such garments are disclosed in U.S. Pat. Nos. 10,016,203 and 10,743,888; in U.S. Pat. Appl. Pub. No. 2008/0221612 A1, in U.S. Pat. Appl. Pub. No. 2013/0267994 A1, in US 2022/0039805 A1, in US 2012/0071917 A1 and in US 2008/0177159 A1, with each garment having particular advantages and disadvantages.

U.S. Pat. Appl. Pub. No. 2013/0267994 A1 or US 2022/0039805 A1, for example, fail to disclose that the cone or (in 2013/0267994: "bulbous portion, protrusion or projection") is, or may be, configured with 'an opening' and fails to disclose any teaching about 'a bolt' (for entering and passing through such an opening), or about 'a bolt disk' (for screwing onto the bolt that would pass through the opening). US2013/0267994 is entirely absent of any teaching that its "occlusion attachment device", the (cone) is, or may be, configured detached or connected to the (cone holder) "platform".

Despite such teachings, there is an on-going need for developing and implementing new and improved garments for temporarily constricting or obstructing an artery for one or more bodily parts, to control bleeding therefrom. There is also a need for developing new and improved garments that are applicable for facilitating temporary arterial obstruction in bodily junctional areas, to control blood flowing therefrom.

SUMMARY OF THE DISCLOSURE

The present disclosure, in some embodiments thereof, relates to devices for temporarily constricting or obstructing an artery for one or more bodily parts, to control bleeding therefrom, and more particularly, but not exclusively, to a compression garment for temporarily constricting or obstructing an artery for the leg, arm or upper limb (neck, shoulder, upper thigh), to control bleeding therefrom, and applications thereof. Some embodiments of the disclosure are applicable for facilitating temporary arterial obstruction in bodily junctional areas, to control blood flowing therefrom.

According to an aspect of some embodiments of the present disclosure, there is provided a compression garment, comprising: a belt comprised of two strips of fabric, a first strip having two belt openings, and a second strip being a smooth fabric; a buckle; a rod and a rod holder configured for holding the rod; wherein the second strip is threaded into the rod, folded in half and enters the first strip along with the rod; a compression unit, comprised of: a cone, a cone bolt, a bolt disk, a cone holder having a cone holder opening, and a bridge configured on upper side of the belt openings; wherein the cone has a cone opening, and is moveable on the bridge, and the cone is configured detached or connected to the cone holder; wherein the cone holder, into which the cone is inserted, is mounted under the bridge directly under the rod holder; wherein the belt is configured for being placed on the bridge, so as to expose the strip and the rod through the belt openings; wherein the rod winds the second strip, so as to develop a tension force on the second strip; and wherein the bridge is configured as a tensioning mechanism into which the winded rod is placed.

According to some embodiments of the disclosure, the cone has an opening, through which the cone bolt may enter and be screwed with the bolt disk to the cone holder.

According to some embodiments of the disclosure, the cone is either detached or connected to the cone holder, according to a type of injury or wound.

According to some embodiments of the disclosure, the cone is fixed so that it exerts pressure on a desired artery, on pressure points, without being fixed to the bridge, and only under the belt.

According to some embodiments of the disclosure, the cone is placed on upper region of a pelvis, in case of injury to an upper thigh or amputation of a leg, or over a subclavian artery, in cases of arm amputation, or injury in a shoulder area.

According to some embodiments of the disclosure, the cone automatically enters a correct place when applying pressure on a femoral artery leading to a leg or on a subclavian artery, leading to a shoulder area, even if an exact location of an artery is not identified.

According to some embodiments of the disclosure, the compression garment further comprises a clock mounted on a clock holder having a clock holder opening mounted on top of the rod holder. According to some embodiments of the disclosure, the clock is a mechanical device configured not to move by itself, and to be set by a therapist or medical assistant. According to some embodiments of the disclosure, the clock includes a hand configured for manually setting a time of initial application of the compression garment. According to some embodiments of the disclosure, the position of the hand is in a 'no move' position on the clock when not used or when the clock is in a fixed position. According to some embodiments of the disclosure, the hand 19a is in a 'raised' position, the hand can be moved, and when the hand is in a 'fixed' position, the hand does not move. According to some embodiments of the disclosure, the hand is configured for making a sound every hour. According to some embodiments of the disclosure, the hand is configured for vibrating when moving, whereby vibrations of the hand are noticeable.

The present disclosure, in some embodiments thereof, relates to devices for temporarily constricting or obstructing an artery for one or more bodily parts, to control bleeding therefrom, and more particularly, but not exclusively, to a compression garment for temporarily constricting or obstructing an artery for the leg, arm or upper limb (neck, shoulder, upper thigh), to control bleeding therefrom, and applications thereof. Some embodiments of the disclosure are applicable for facilitating temporary arterial obstruction in bodily junctional areas, to control blood flowing therefrom.

All technical or/and scientific words, terms, or/and phrases, used herein have the same or similar meaning as commonly understood by one of ordinary skill in the art to which the disclosure pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the disclosure, exemplary methods, apparatuses, equipment, and materials, are illustratively described below. In case of conflict, the patent specification, including definitions, will control.

BRIEF DESCRIPTION OF THE SEVERAL VIEWS OF THE DRAWINGS

Some embodiments of the present disclosure are herein described, by way of example only, with reference to the accompanying drawings and photographs. With specific reference now to the drawings and photographs in detail, it is stressed that the particulars shown are by way of example and for purposes of illustrative description of some embodiments of the present disclosure. In this regard, the description taken together with the accompanying drawings and photographs make apparent to those skilled in the art how some embodiments of the present disclosure may be practiced.

In the drawings and photographs.

DESCRIPTION OF SPECIFIC EMBODIMENTS OF THE DISCLOSURE

The present disclosure, in some embodiments thereof, relates to a compression garment for temporarily constricting or obstructing an artery for the leg, arm or upper limb (neck, shoulder, upper thigh), to control bleeding therefrom, and applications thereof. Some embodiments of the disclosure are applicable for facilitating temporary arterial obstruction in bodily junctional areas, to control blood flowing therefrom.

Implementation of the present disclosure attempts to address, and overcome, at least some of the on-going limitations and problems associated with temporarily constricting or obstructing an artery for the leg, arm or upper limb (neck, shoulder, upper thigh), to control bleeding therefrom. In exemplary embodiments, the compression garment is easy to carry, is not cumbersome, and the time required to apply it is relatively very short.

For purposes of further understanding exemplary embodiments of the present disclosure, in the following illustrative description thereof, reference is made to the drawings.

Throughout the following description and accompanying drawings, same reference numbers refer to same objects, components, elements, or features. It is to be understood that the disclosure is not necessarily limited in its application to particular details of construction or/and arrangement of exemplary device or apparatus components, set forth in the following illustrative description. The disclosure is capable of having other exemplary embodiments, or/and of being practiced or carried out in various alternative ways.

Figure 18:
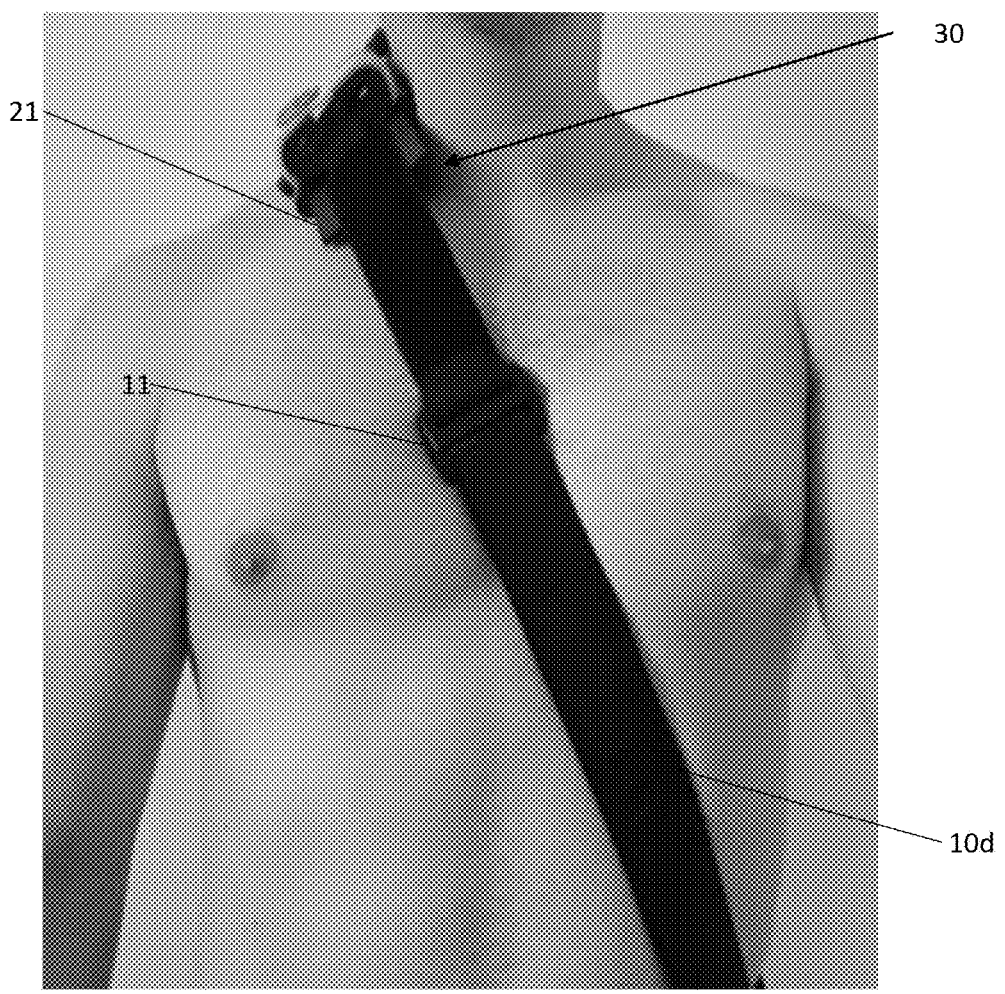
FIG. 18 is a photograph showing exemplary applications of the compression garment for facilitating arterial obstruction in a junctional area (neck area), in accordance with some embodiments of the disclosure.

Exemplary embodiments of the herein disclosed compression garment are employed for at least the following three applications: (i) normal arterial obstruction in a limb; (ii) performing pressure on a pressure points 31 over the femoral artery (in cases of amputation of a leg, or injury to the upper thigh) (FIG. 19); and (iii) performing pressure on pressure points 30 over the subclavian artery (in cases of arm amputation, or injury in the shoulder area) (FIG. 18).

Figure 1:
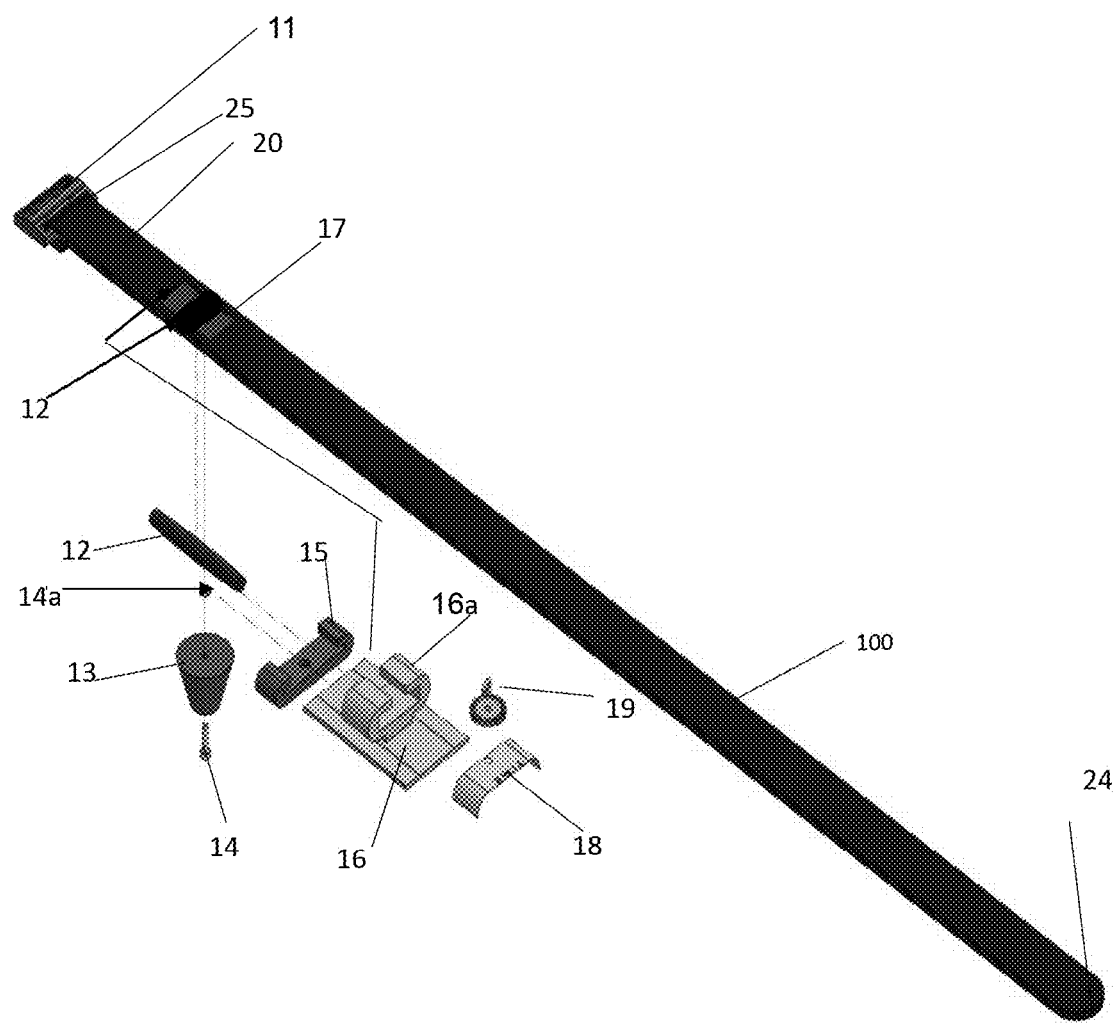
FIG. 1 is a schematic partly exploded perspective view of an exemplary embodiment of the compression garment, in accordance with some embodiments of the disclosure.

With reference to FIG. 1, in exemplary embodiments, the compression garment includes a belt 100 and a compression unit 21 configured to function in a tourniquet-like manner. In exemplary embodiments, the belt 100 includes two strips of fabric (strip 10 and strip 17), and a buckle 11. In exemplary embodiments, the unit 21 includes a bridge 16, a cone 13, a cone bolt 14, a bolt disk 14a, a cone holder 15, a clock 19, a clock holder 18, and a rod 12.

Figure 8:
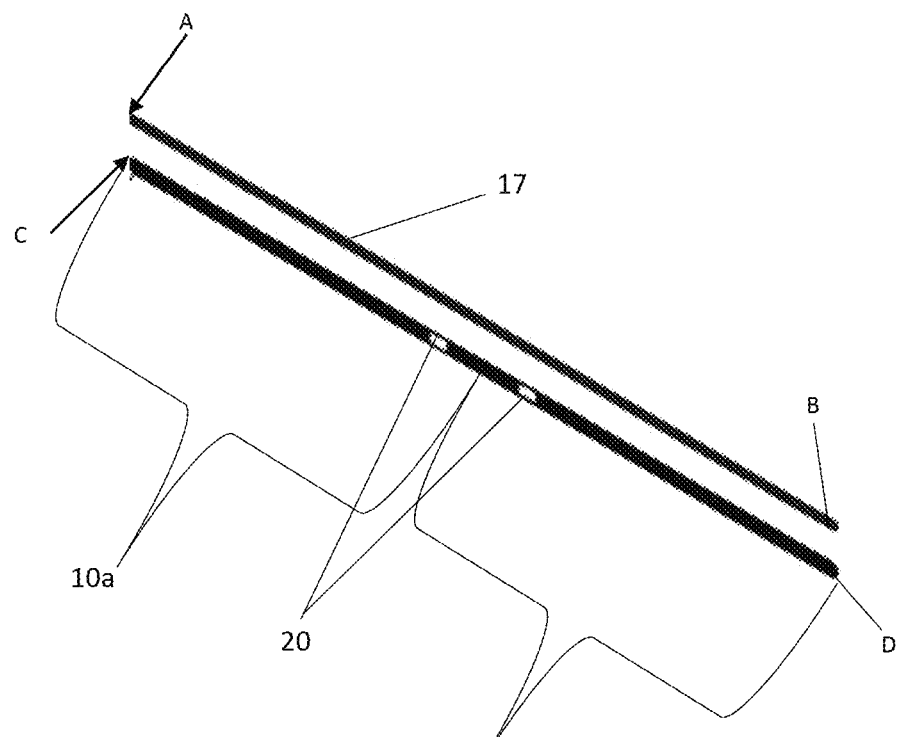
FIG. 8 is a schematic perspective view of exemplary embodiments of the inner strip, the outer strip, the division, and the openings of the outer strip, in accordance with some embodiments of the disclosure.

In exemplary embodiments, the belt 100 includes two strips of fabric (FIG. 8), being an outer strip 10 and an inner strip 17. The strip 17 is slightly smaller than the strip 10. In exemplary embodiments, the strip 10 is divided into two parts 10a and 10b. In exemplary embodiments, part 10a is a smooth fabric, and part 10b is made of scotch fabric or any other type of fabric that can connect to another fabric.

In exemplary embodiments, the strip 10 has two openings 20, configured so that rod 12 can fit therethrough. When the strip 10 is folded, the two openings 20 are parallel to one another (FIGS. 9 and 10).

Figure 7:
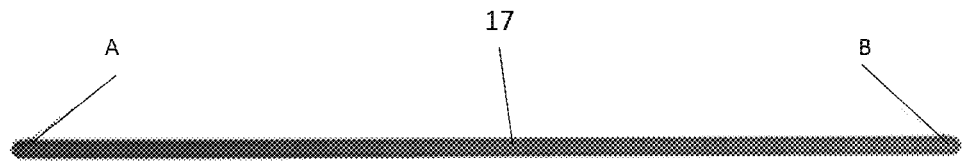
FIG. 7 is a schematic side view of an exemplary embodiment of the inner strip in accordance with some embodiments of the disclosure.

In exemplary embodiments, the strip 17 is smooth with no openings being the inner part of the belt 100 (FIG. 7). In exemplary embodiments, the strip 17 is threaded into rod 12, folded in half and enters strip 10 along with the rod that emerges from the openings 20.

Figure 9:
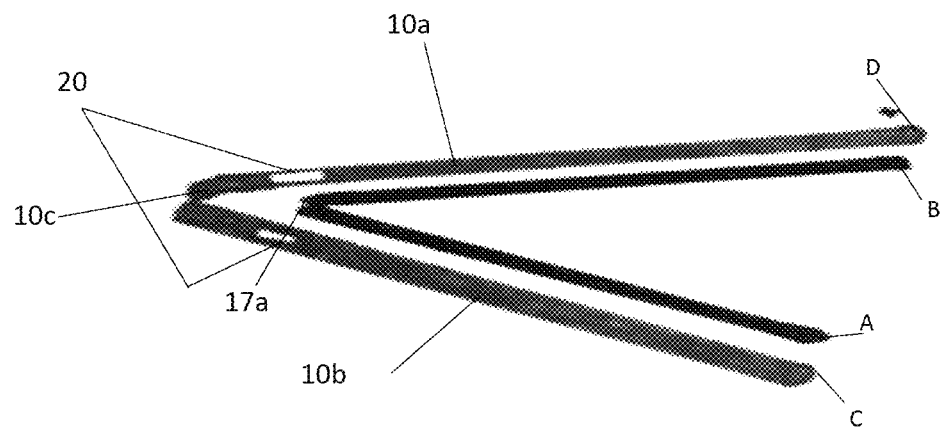
FIG. 9 is a schematic perspective view of an exemplary embodiment of the folded strips, the meeting points of the openings and the position of the inner strip relative to the outer strip, in accordance with some embodiments of the disclosure.
Figure 10:
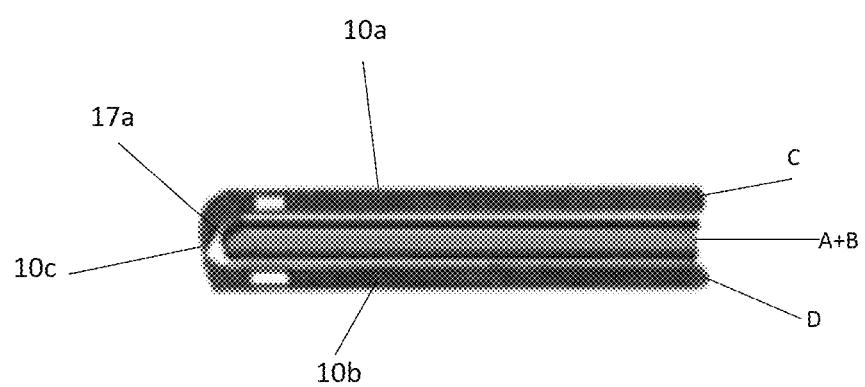
FIG. 10 is a schematic transparent side view of an exemplary embodiment of the folded belt before seaming of the open edges A-D, in accordance with some embodiments of the disclosure.
Figure 11:
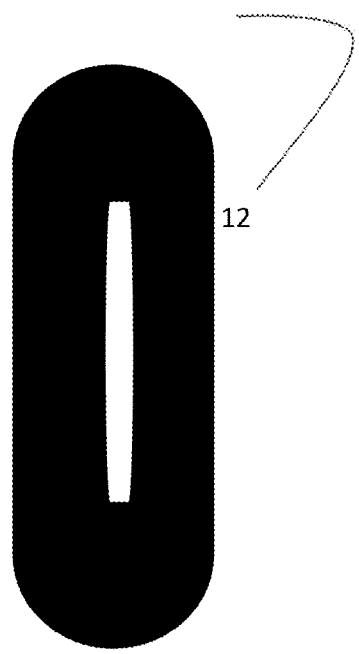
FIG. 11 is a schematic diagram of an exemplary embodiment of the rod, in accordance with some embodiments of the disclosure.
Figure 12:
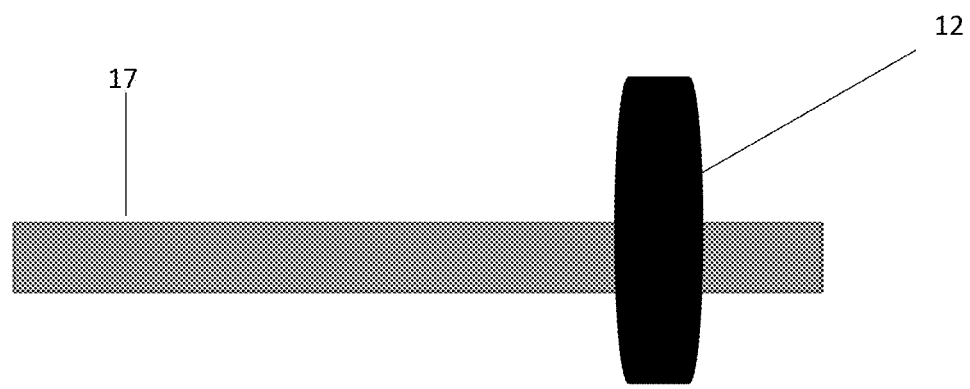
FIG. 12 is a schematic diagram of an exemplary embodiment of the rod being threaded into the inner strip, in accordance with some embodiments of the disclosure.

In exemplary embodiments, the folded side of the strip 17 (17a) rests inside the strip 10 close to the folded side of the strip 10 (10c), as shown in FIGS. 9 and 10. In exemplary embodiments, the open ends of the strip 10 (C & D) and the open ends of the strip 17 (A & B) face the same side.

Figure 15:
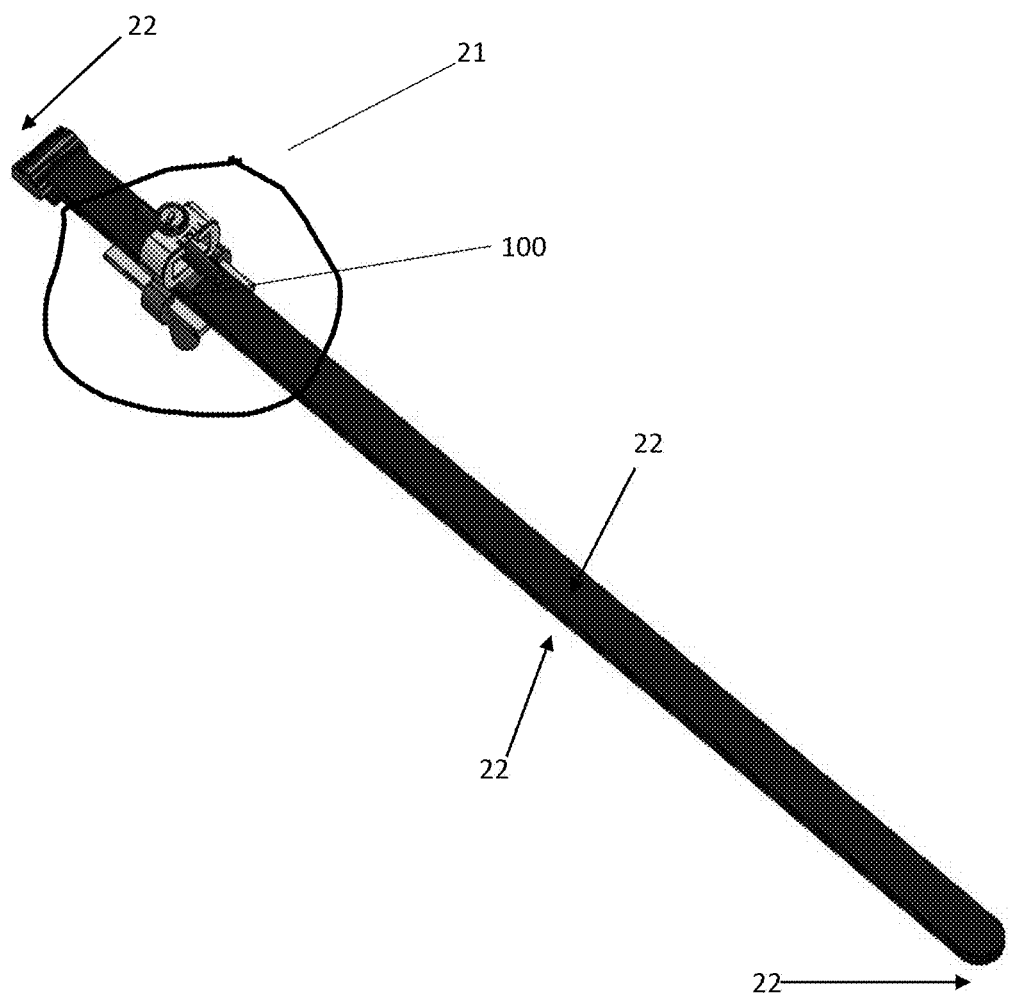
FIG. 15 is a schematic perspective view of an exemplary embodiment of the assembled and seamed strips, highlighting the position of the compression garment unit, in accordance with some embodiments of the disclosure.
Figure 16:
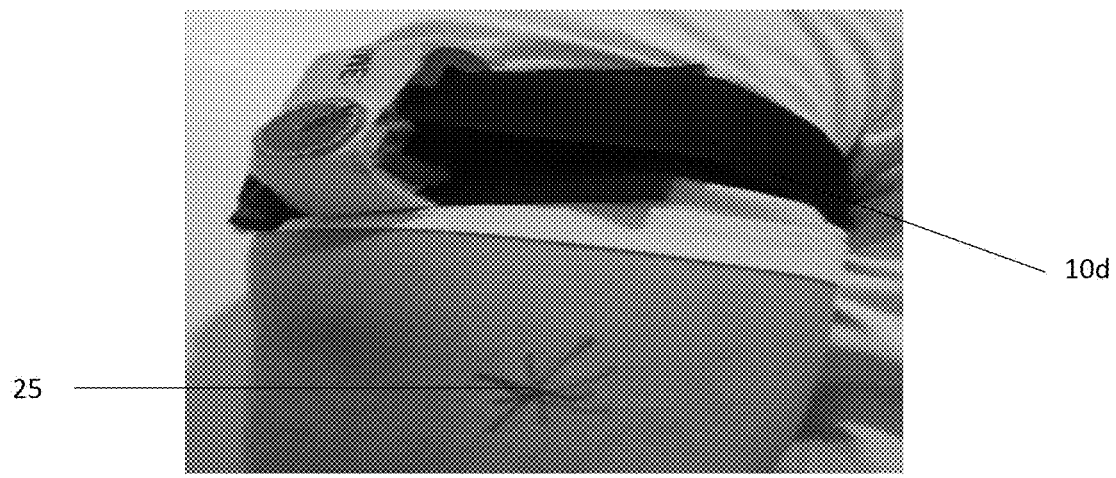
FIG. 16 is a photograph showing exemplary application of the compression garment in case of massive bleeding from a limb (arm), in accordance with some embodiments of the disclosure.
Figure 17:
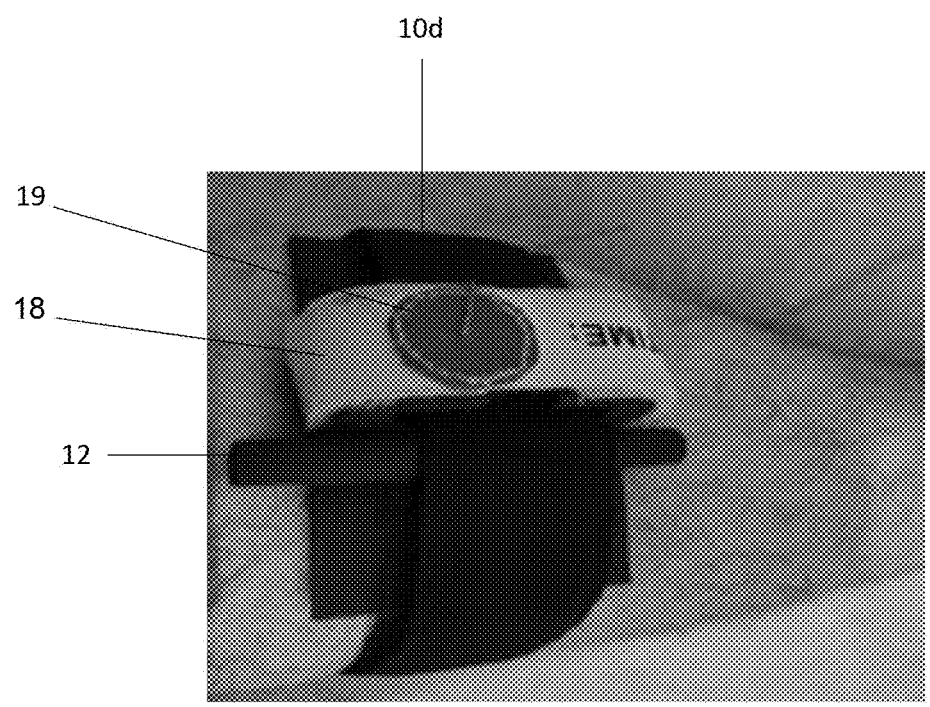
FIG. 17 is a photograph showing exemplary applications of the compression garment in case of massive bleeding from a limb (leg), in accordance with some embodiments of the disclosure.

In exemplary embodiments, once the folded strip 17 and the rod 12 are in place, the strip 10 is seamed all around as shown in FIG. 15 (all along edges 22) including edges A-D 24 (FIG. 1) into one belt 100. In exemplary embodiments, the belt 100 is placed on the bridge 16, thereby exposing the strip 17 and the rod 12 through the openings 20 (FIG. 1).

Figure 2:
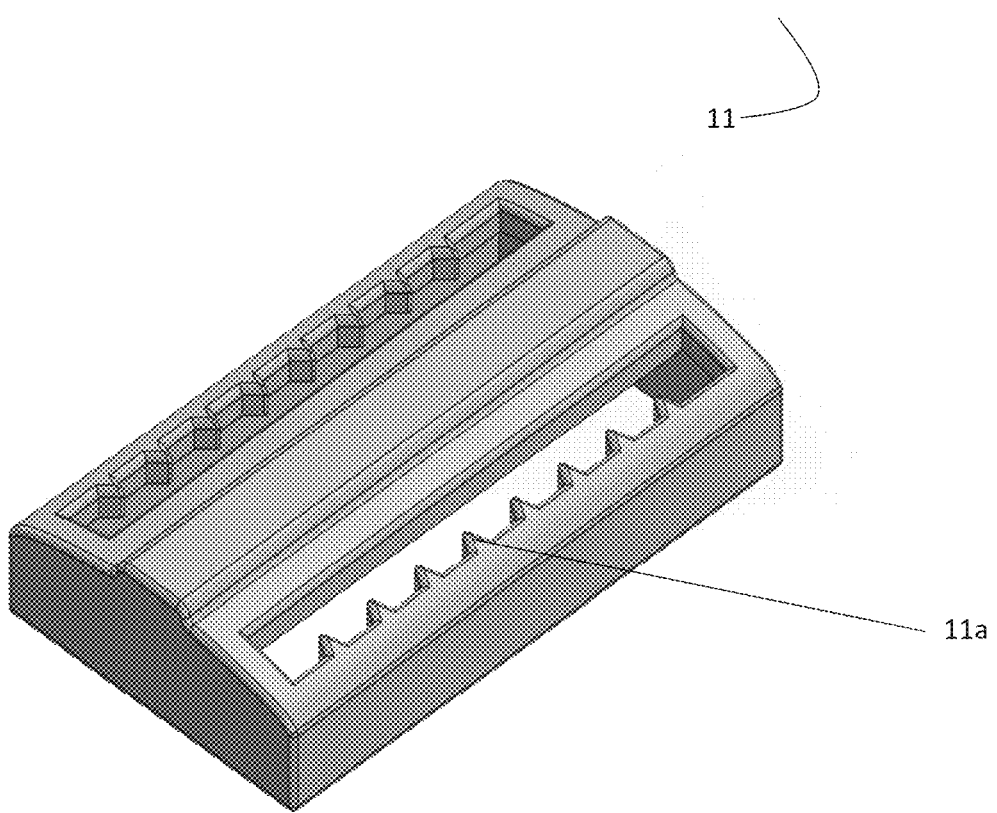
FIG. 2 is a schematic perspective view of an exemplary embodiment of the buckle and inner teeth thereof, in accordance with some embodiments of the disclosure.

In exemplary embodiments, the belt 100 has a first end 25 and a second end 24. In exemplary embodiments, the first end 25 is looped through the buckle 11. In exemplary embodiments, the buckle 11 has kind of 'teeth' 11a that grab the first end 25 of the belt 100 and keeps the belt 100 fixed (FIG. 2).

Figure 3:
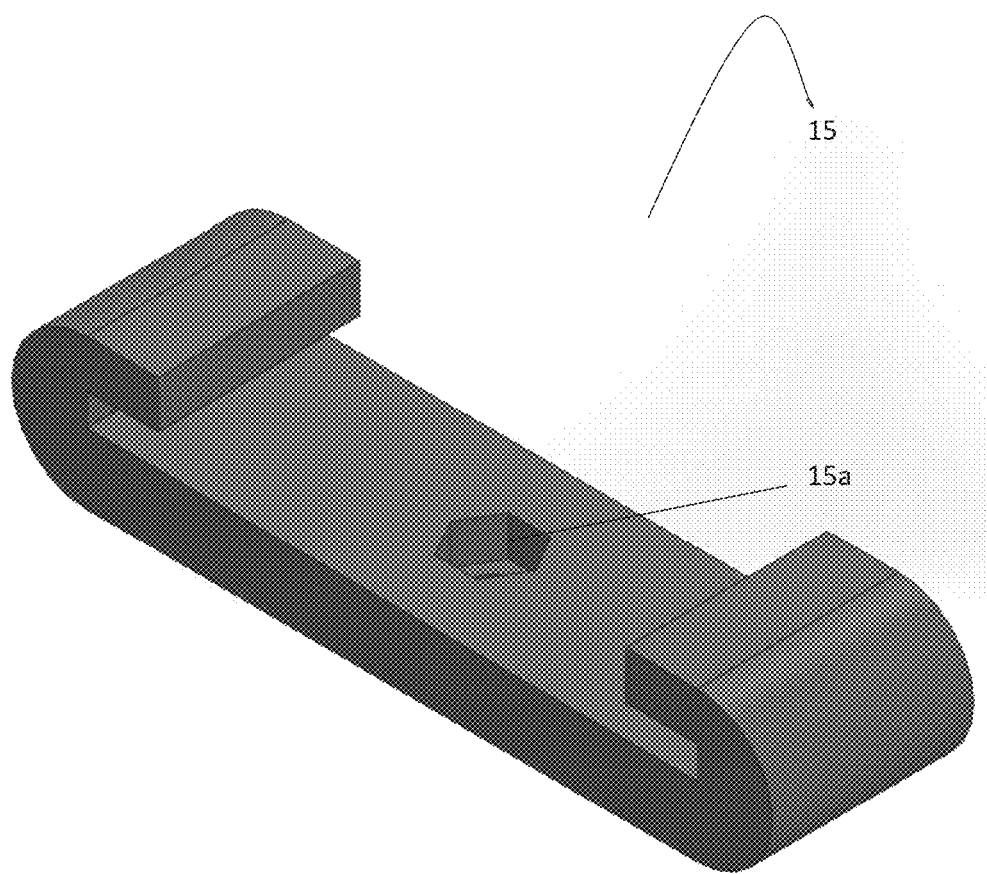
FIG. 3 is a schematic perspective view of an exemplary embodiment of the bridge that holds the cone, in accordance with some embodiments of the disclosure.
Figure 4:
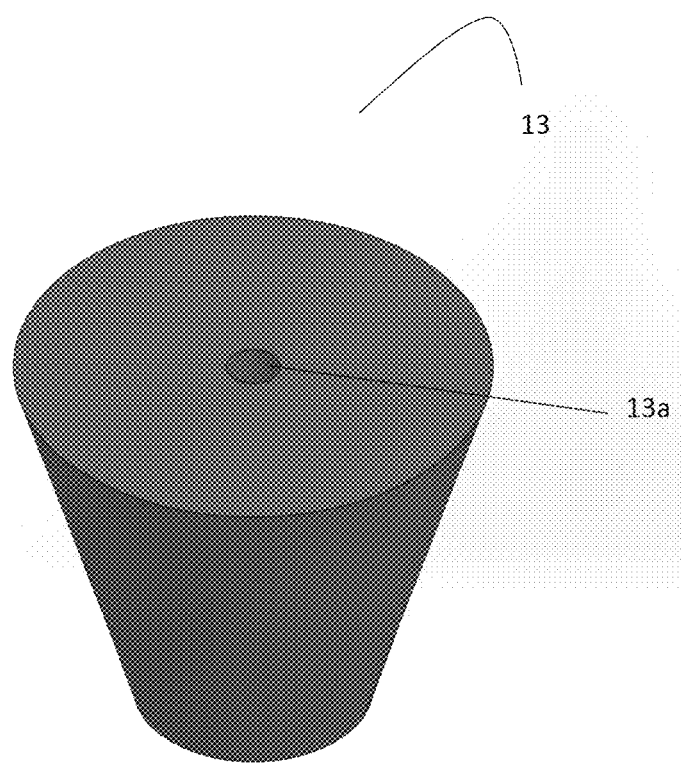
FIG. 4 is a schematic perspective view of an exemplary embodiment of the cone, in accordance with some embodiments of the disclosure.
Figure 5:
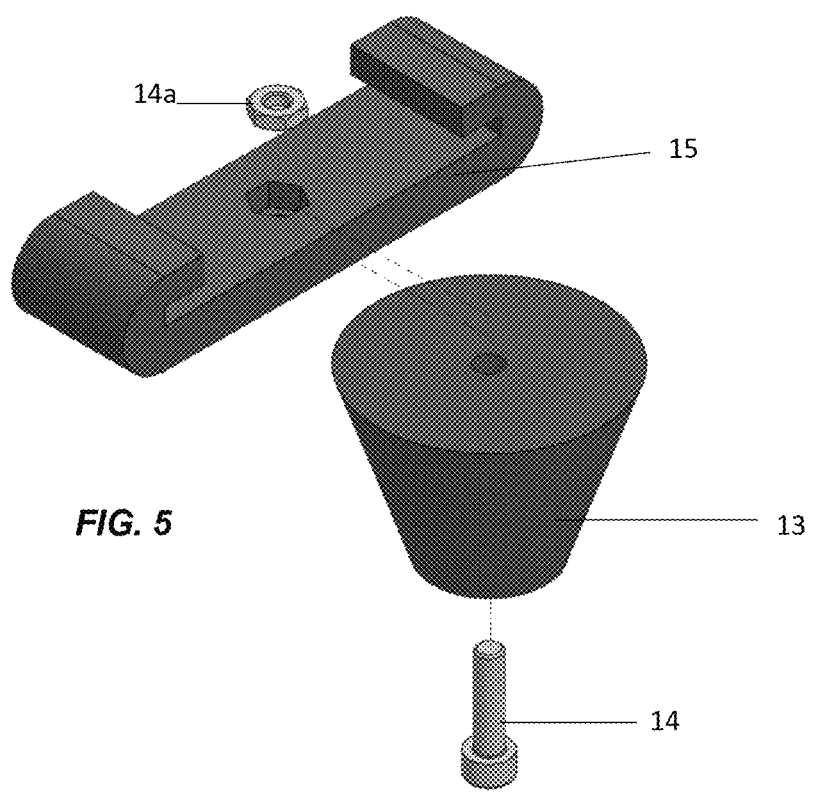
FIG. 5 is a schematic exploded view of an exemplary embodiment of the bridge, the cone, the bolt and the bolt disk, in accordance with some embodiments of the disclosure.
Figure 6:
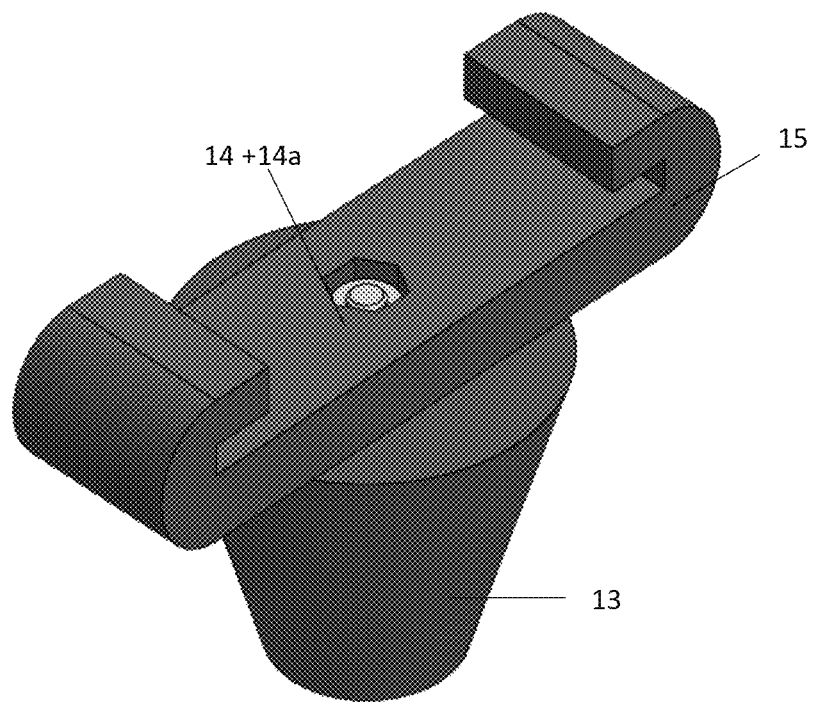
FIG. 6 is a schematic perspective view of an exemplary embodiment of the assembled bridge with the cone and the bolt disk, in accordance with some embodiments of the disclosure.

FIG. 3 shows an exemplary embodiment of the cone holder 15 having an opening 15a for cone bolt 14, attaching cone 13 to the cone holder 15. In exemplary embodiments, the cone 13 (FIG. 4) has an opening 13a, through which the cone bolt 14 may enter and be screwed with the bolt disk 14a to the cone holder 15 (FIGS. 5 and 6).

In exemplary embodiments, the cone 13 is configured to exert pressure on the desired artery. In exemplary embodiments, the cone 13 is dynamic (i.e., translatable, moveable) on and along the bridge 16. In alternative exemplary embodiments, the cone 13 is fixed as explained above, and static at a selected position (location) along the bridge 16. In exemplary embodiments, the cone 13 can be either detached or connected as described above, according to the particular type of injury and wound. In exemplary embodiments, the cone 13 is fixed, so as to exert pressure on the desired artery (for example, pressure points 30 or 31), without being fixed to the bridge 16, but only under the belt 100.

Figure 19:
FIG. 19 is a photograph showing exemplary applications of the compression garment for facilitating arterial obstruction in a junctional area (upper thigh or pelvis area), in accordance with some embodiments of the disclosure.
Figure 20:
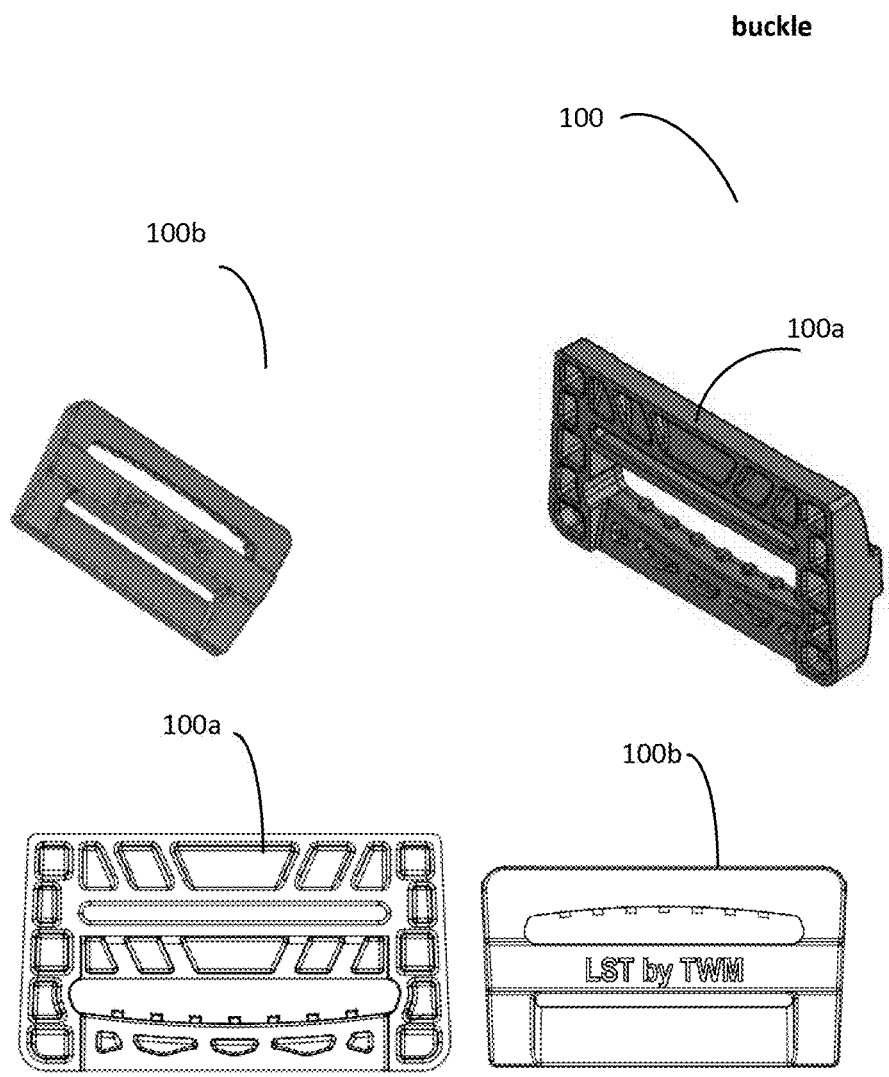
FIG. 20 is a schematic partly exploded perspective, rear and front view of an exemplary buckle and inner teeth thereof, in accordance with some embodiments of the disclosure.

In exemplary embodiments, in case of injury to the upper thigh or amputation of a leg, the cone 13, being an integral part of the belt 100, is placed on the upper region of the pelvis, (FIG. 19). This position ensures that even if the therapist does not identify the exact location of the artery (pressure point 31), then, when applying pressure, the cone 13 automatically enters the correct place (pressure point 31), pressing the femoral artery leading to the leg, as depicted in FIG. 19.

In exemplary embodiments, the bridge 16 is placed on the upper side of the opening 20, leaving room for the rod 12, as shown in FIG. 1.

In exemplary embodiments, the rod 12 winds the strip 17 so as to develop a tension force on the inner strip 17. When the needed tension is achieved, the rod 12 is placed through the pincers 16a1 and 16a2 in the rod holder 16a (FIG. 14).

In exemplary embodiments, the bridge 16 acts as a tensioning mechanism, into which the winding rod 12 is placed so as to maintain the tension after the rod 12 winds the strip 17.

Figure 13:
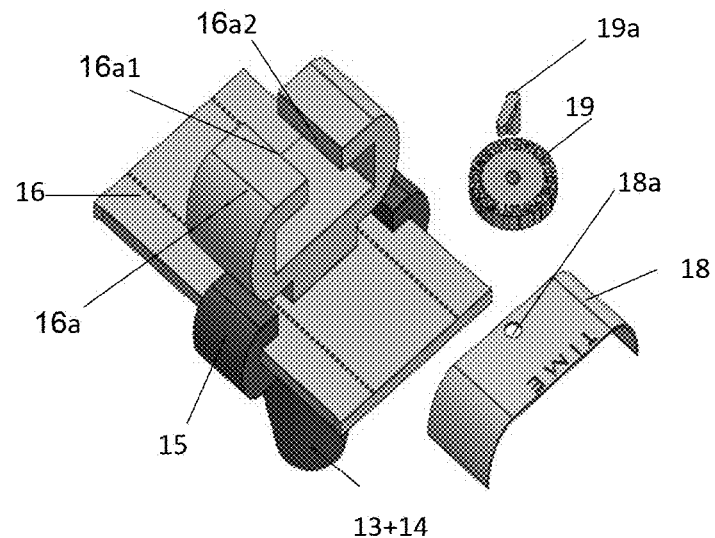
FIG. 13 is a schematic partly exploded perspective view of an exemplary embodiment of the compression unit, in accordance with some embodiments of the disclosure.
Figure 14:
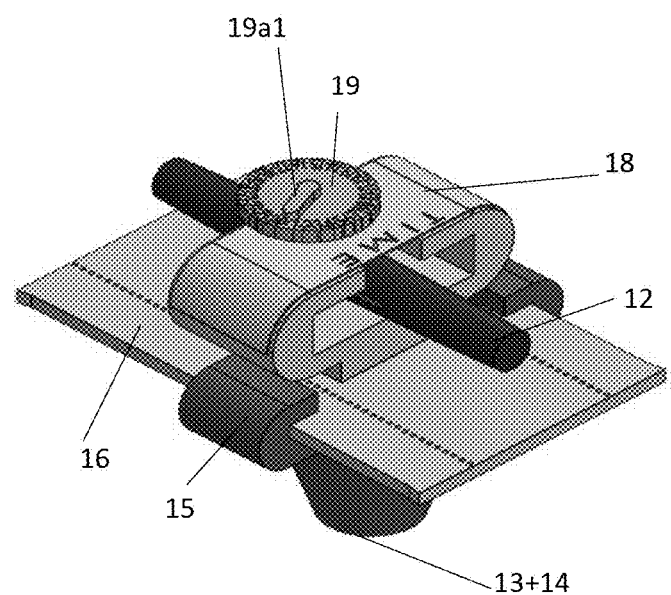
FIG. 14 is a schematic perspective view of an exemplary embodiment of the assembled compression garment unit, in accordance with some embodiments of the disclosure.

As shown in FIGS. 13 and 14, in exemplary embodiments, the cone holder 15, into which the cone 13 is inserted, is mounted under the bridge 16 and directly under the rod holder 16a, in such a way that the cone 13 is located in the center of the bridge 16.

In exemplary embodiments, the clock holder 18 is mounted on top of the rod holder 16a. In exemplary embodiments, the clock holder 18 has an opening 18a on which the clock 19 is mounted. In exemplary embodiments, the clock holder 18 covers the space between the pincers 16a1 and 16a2.

In some aspects the compression garments of this disclosure should generally remain inflated a maximal time of 1.5 to 2 hours, the time in which most wounded people can get to a hospital. Therefore, having a compression garment according to this disclosure in place for two or fewer hours should not have any ill effects beyond those caused by the injury requiring the compression garment. A compression garment, such as a tourniquet, that continues to restrict flow often leads to deep vein thrombosis (DVT), a dangerous and life-threatening complication that can cause permanent injury, even death.

Writing the time (of initial application of the garment) on the garment is customary today, but it involves taking the risk that the time may be erased, become unintelligible, or ignored.

In exemplary embodiments, the clock 19, as shown in FIGS. 13 and 14, is included in the unit 21. In exemplary embodiments, the clock 19 is a mechanical device being set by the therapist or any other medical assistant and does not move by itself. In exemplary embodiments, the clock 19 includes a hand 19a configured for setting the time of application by a therapist or medical assistant who puts the garment on a wounded person.

In exemplary embodiments, the position of the hand 19a is in a 'no move' position on the clock 19, when not used or when the clock 19 is in a fixed position 19a1 (FIG. 14). In exemplary embodiments, when the hand 19a is in a 'raised' position (FIG. 13), the hand 19a can be moved. In exemplary embodiments, when the hand 19a is in a fixed position 19a1, the hand 19a cannot move, even by accident.

In exemplary embodiments, the clock 19 and the hand 19a thereof are configured so as to record the time when the garment was initially fixed at the wound area. In exemplary embodiments, it is possible to hear a dial, for example, when the hand 19a is moved (after the hand 19a was lifted). In exemplary embodiments, for every hour the clock 19 makes a sound and the movements between hours are heard or felt, so that time of garment application may be set even in very difficult or dangerous situations (for example, during darkness, or under combat fire).

With reference to FIGS. 20-27, in exemplary embodiments, the exemplary compression garment 800 includes belts 500 and belt 600. Both belts comprise two strips of fabric (outer strip 500a and inner strip 500b) and a buckle 100.

In exemplary embodiments, the unit 800 includes a bridge 300, a pressure pin 400, a rod 200, and a buckle 100.

In exemplary embodiments, the belt 500 includes two strips of fabric (FIG. 5), being an outer strip 500a and an inner strip 500b. The strip 500a is slightly smaller than the strip 500b. In exemplary embodiments, part 500a is a smooth fabric, and part 500b is made of scotch fabric or any other type of fabric that can connect to another fabric.

In exemplary embodiments, belt 500 has a cutting mark point 500c for shortening the strip. In exemplary embodiments, the strip 600 has a cutting mark point 600a for shortening the strip.

In exemplary embodiments, belts 500 or 600 are smooth with no openings. strip 500b is threaded into rod 200.

In exemplary embodiments, the folded strip 500b and is threaded into rod 200. In exemplary embodiments, the belt 500 (or 600) is placed on bridge 300.

Figure 21:
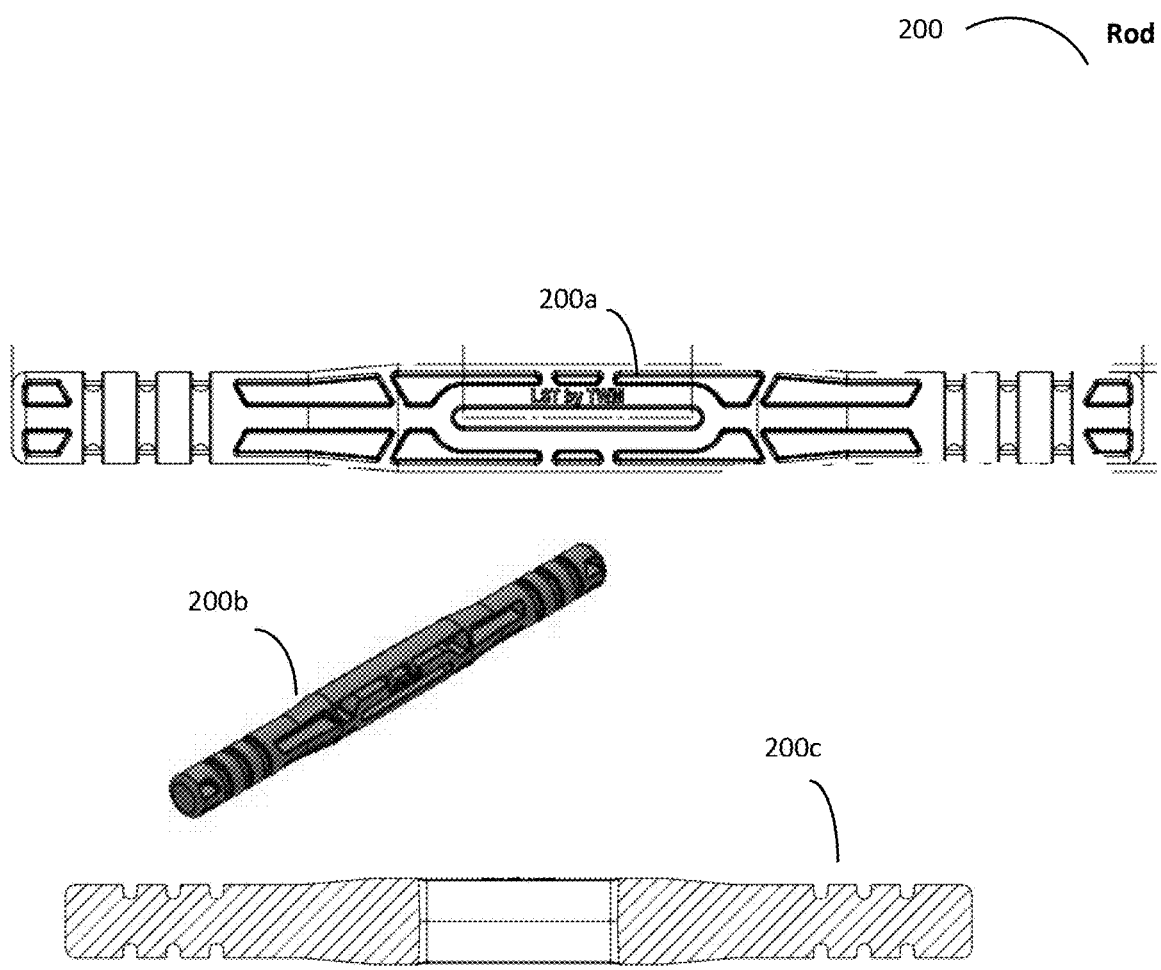
FIG. 21 is a schematic perspective, front and rear views of an exemplary embodiment of the rod, in accordance with some embodiments of the disclosure.

In exemplary embodiments, buckle 100 has kind of 'teeth' that grab belt 500 (or 600) and keeps the belts fixed (FIG. 21).

Figure 22:
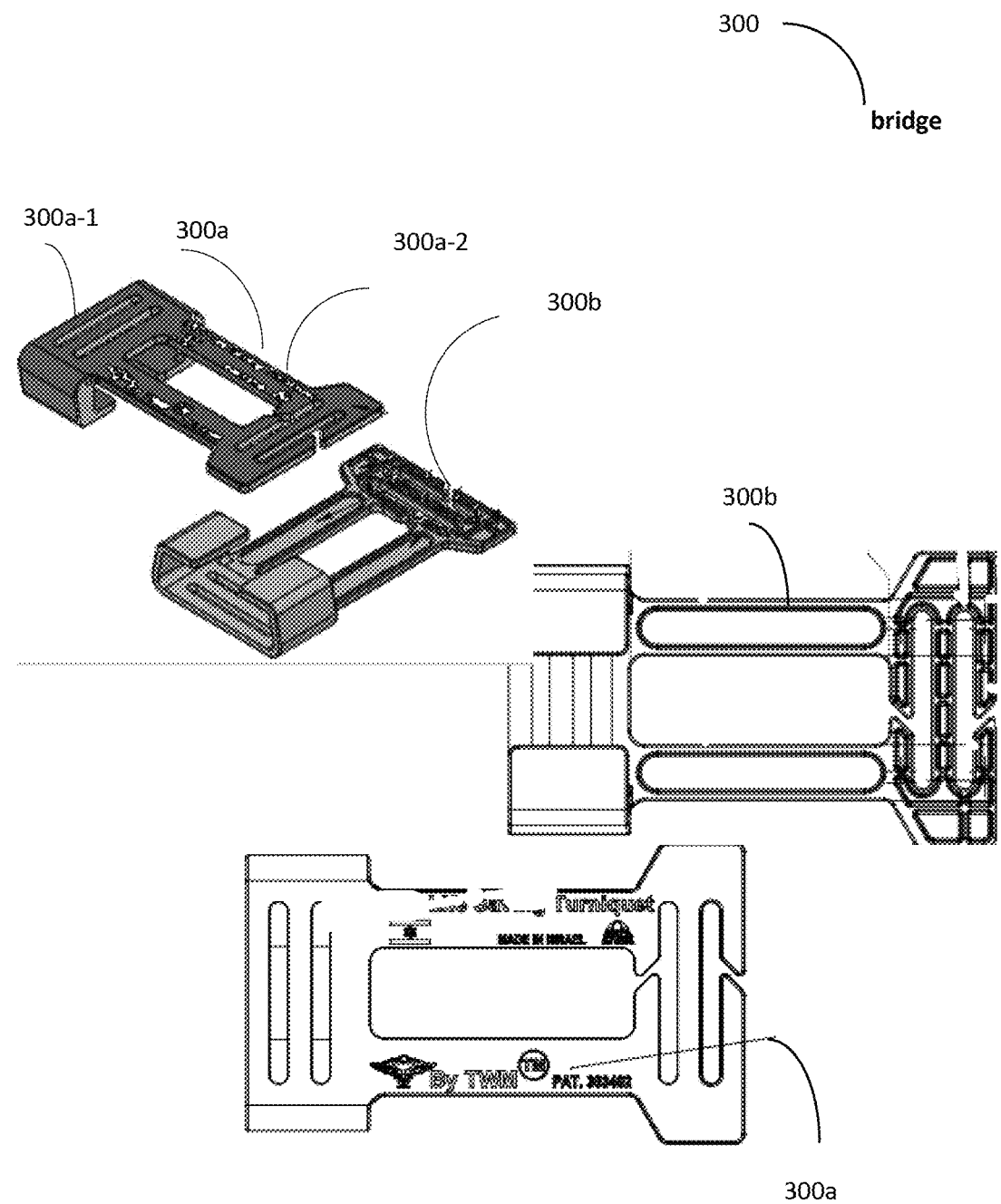
FIG. 22 is a schematic perspective, front and rear views of an exemplary embodiment of the bridge that holds the pressure pin, in accordance with some embodiments of the disclosure.
Figure 23:
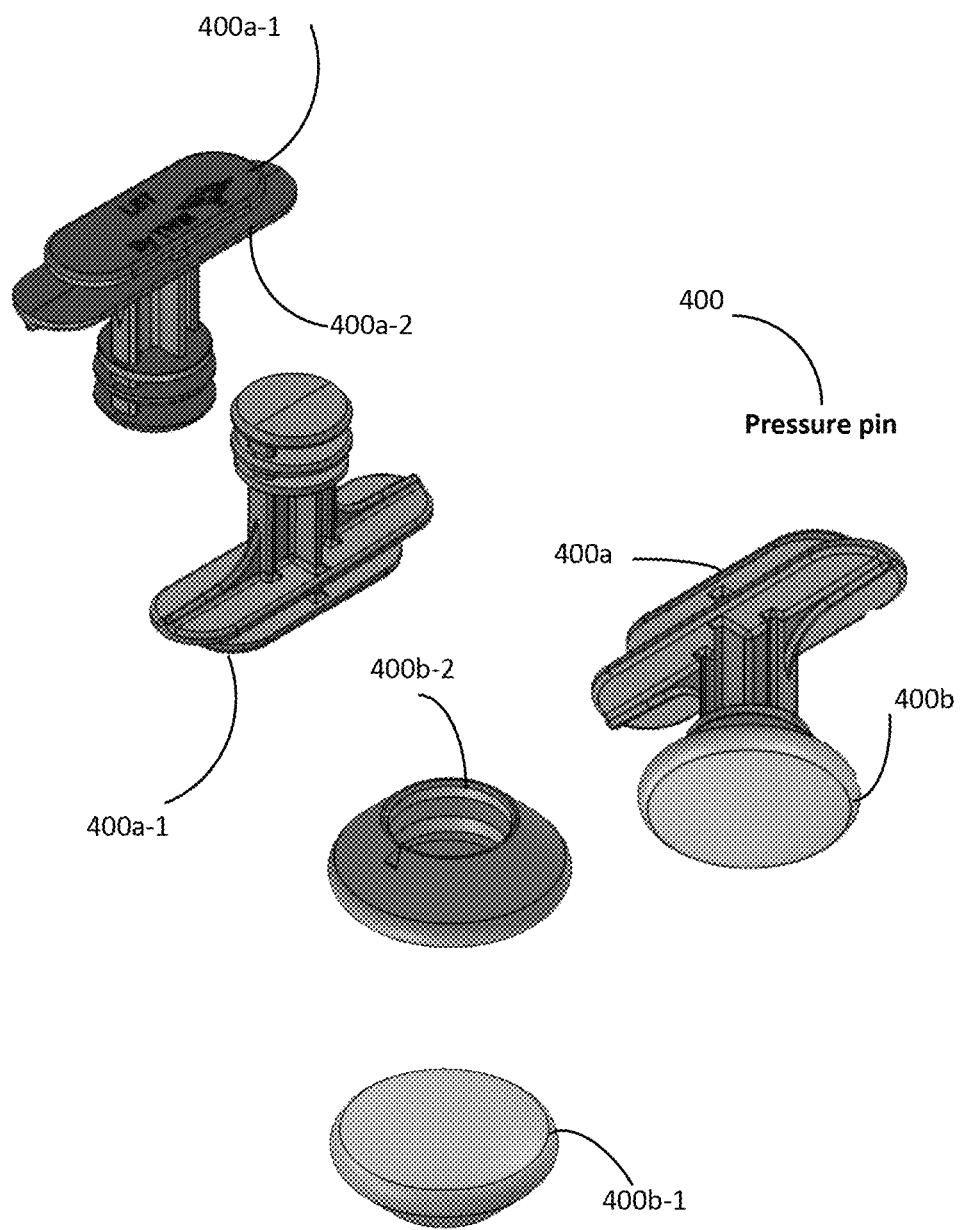
FIG. 23 is a schematic perspective view of an exemplary embodiment of the pressure pin and its parts, in accordance with some embodiments of the disclosure.
Figure 24:
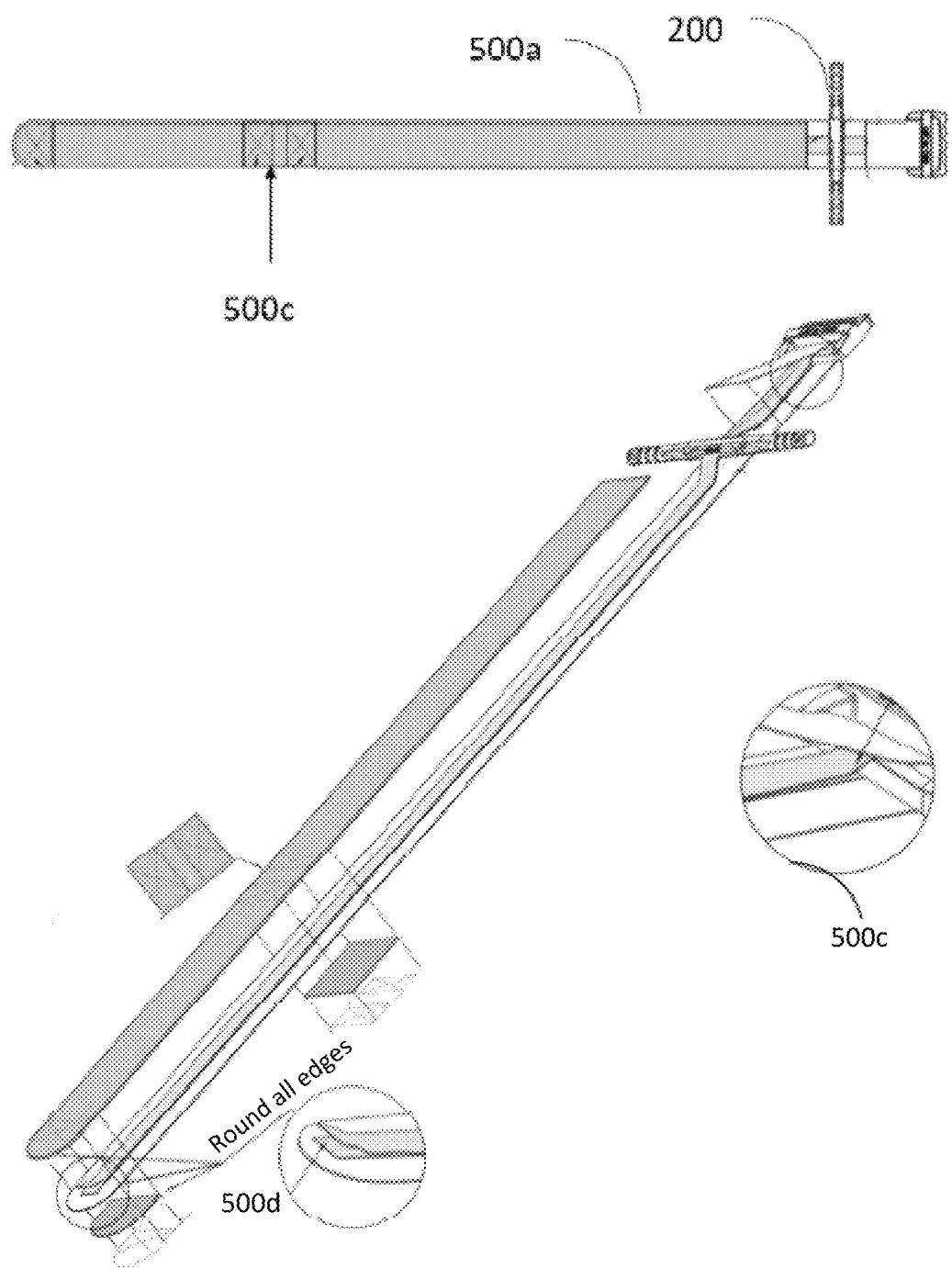
FIG. 24 is a schematic front and exploded views of an exemplary embodiment of the strip in accordance with some embodiments of the disclosure.
Figure 25:
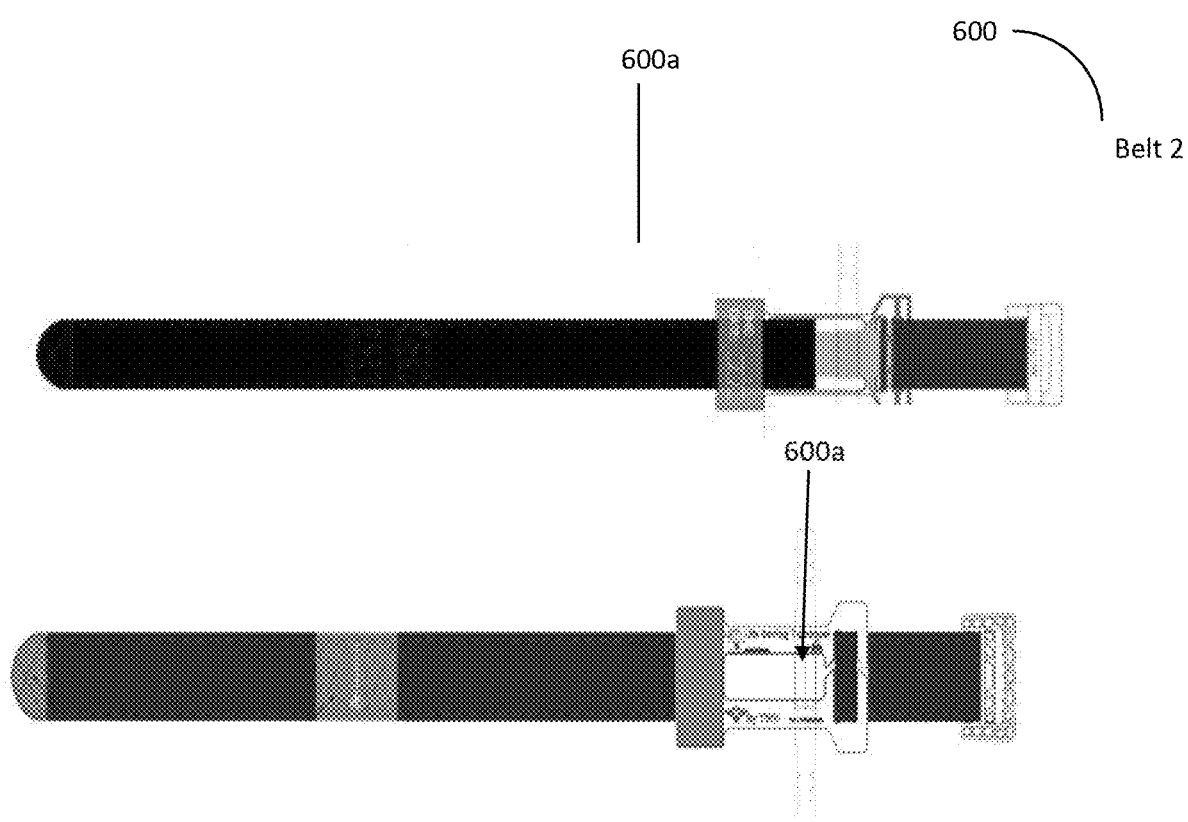
FIG. 25 is a schematic perspective view of another exemplary embodiment of the strip, the outer strip, the division points, and the openings of the strip, in accordance with some embodiments of the disclosure.
Figure 26:
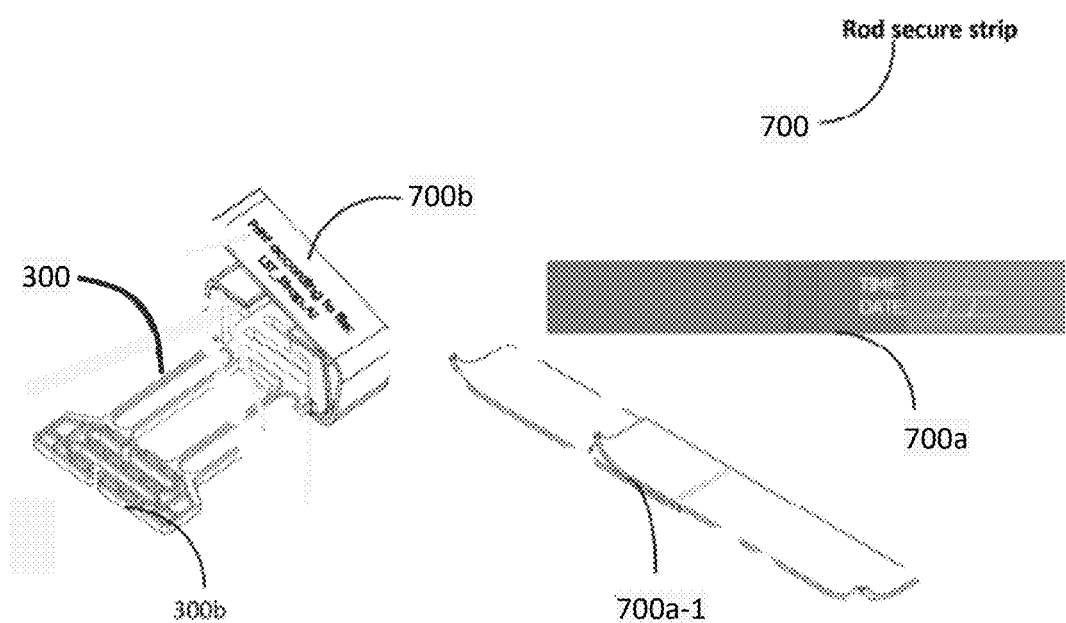
FIG. 26 is an illustration of an exemplary embodiment of the rod secure strip, in accordance with some embodiments of the disclosure.

FIG. 22 shows an exemplary embodiment of pressure pin 400. The pressure pin 400 consists of: a closing lever 400b, which also consists of two parts 400b-1 and 400b-2. The closing lever 400b, which consists of two plastic plates or other hard material (400a-1, 400a-2). Between the two plates there is a gap. Plate 400a-1 rotates on an axis and moves inside bridge 300 (see FIG. 13).

In exemplary embodiments, the pressure pin 400 is configured to exert pressure on the desired artery. In exemplary embodiments, the pressure pin 400 is dynamic (i.e., translatable, moveable) on and along bridge 300.

In exemplary embodiments, pressure pin 400 can be either detached or connected as described above, according to the particular type of injury and wound. In exemplary embodiments, pressure pin 400 is fixed, so as to exert pressure on the desired artery, without being fixed to bridge 300, but only under belt 500 (or 600).

Figure 33:
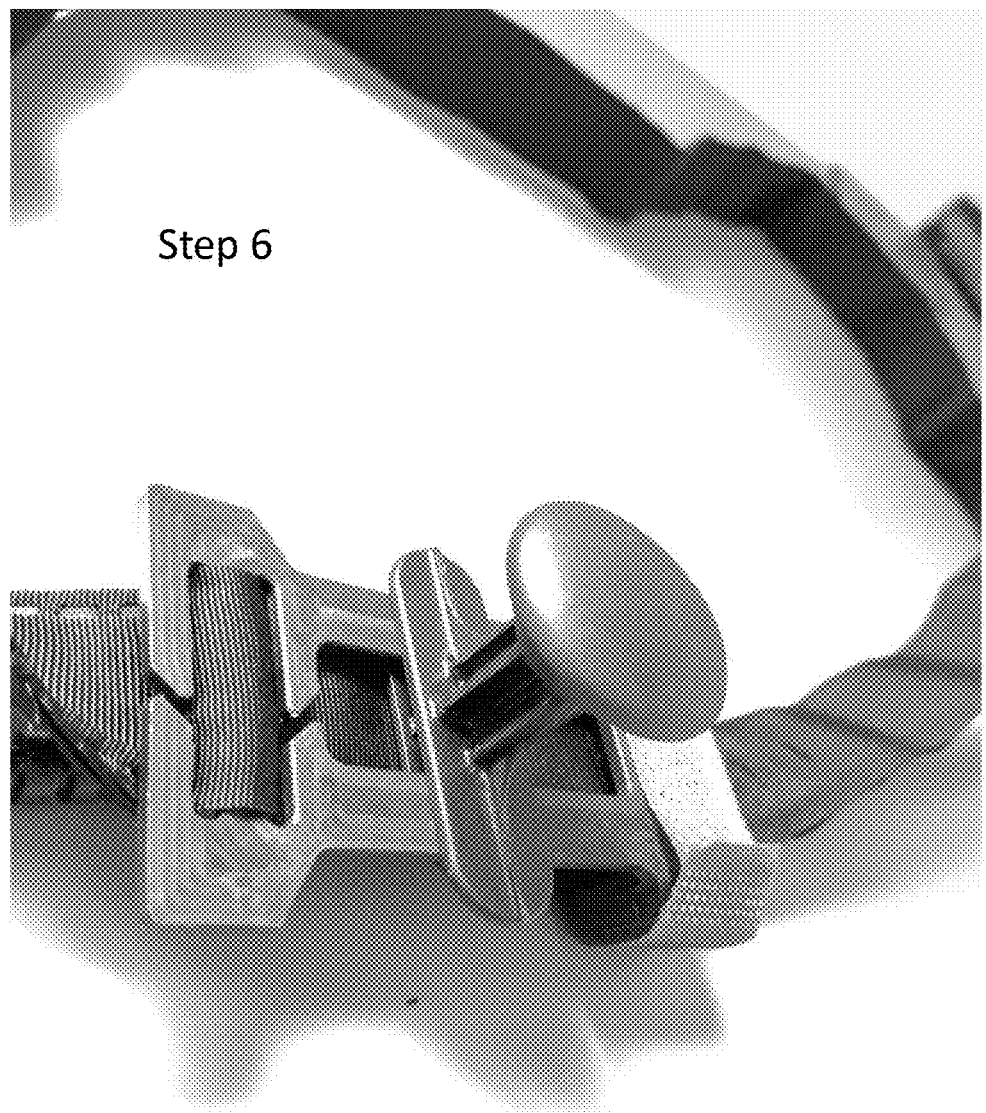
FIG. 33 is a picture of the rode secure strip and the pressure pin showing step 6 of the assembling method.

In exemplary embodiments, the bridge 300 is placed on the upper side of the belt 500 (or 600), leaving room for rod 200, as shown in FIG. 33.

Figure 34:
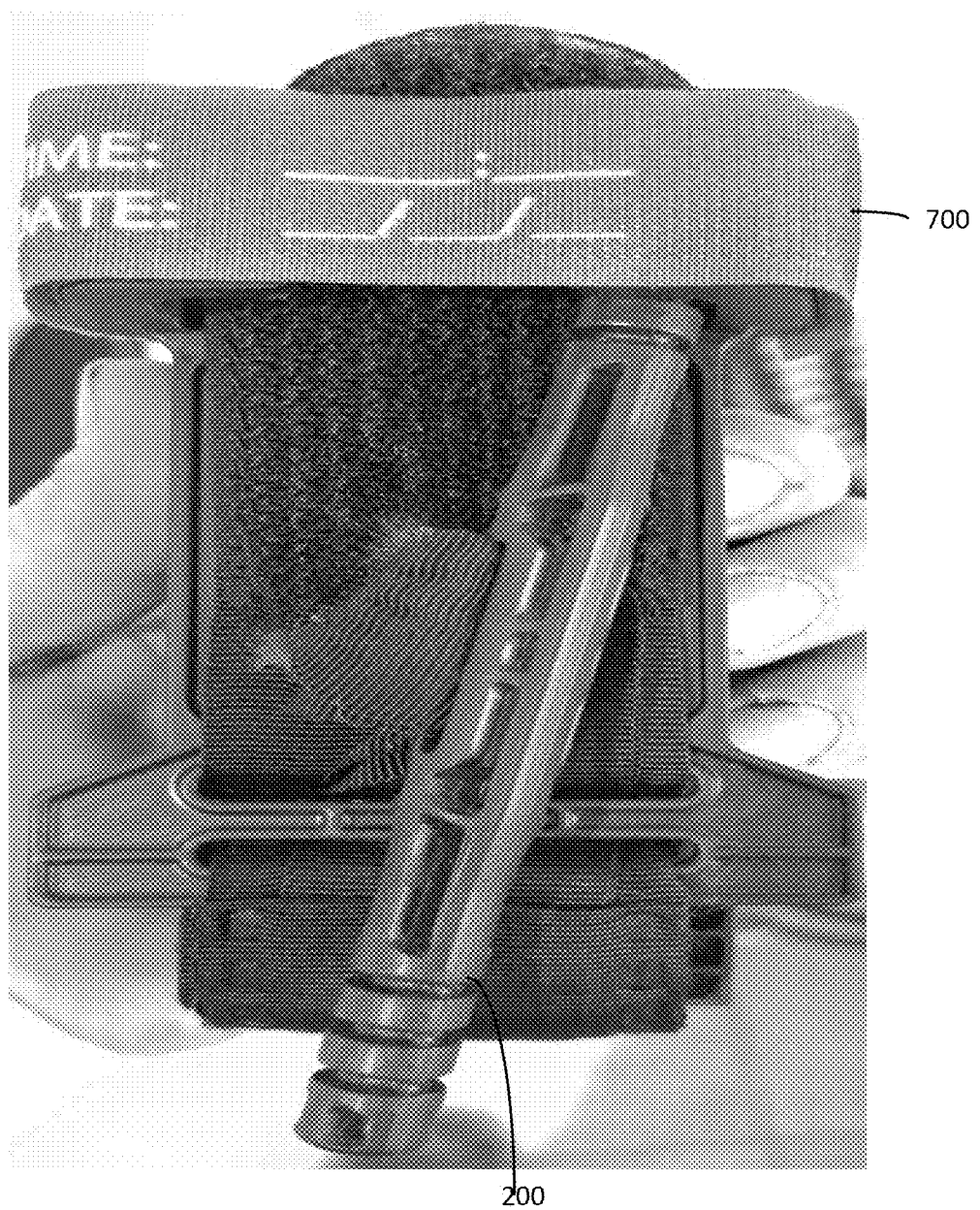
FIG. 34 is a picture demonstrating the placing of the rod when the compression garment is in use.
Figure 35:
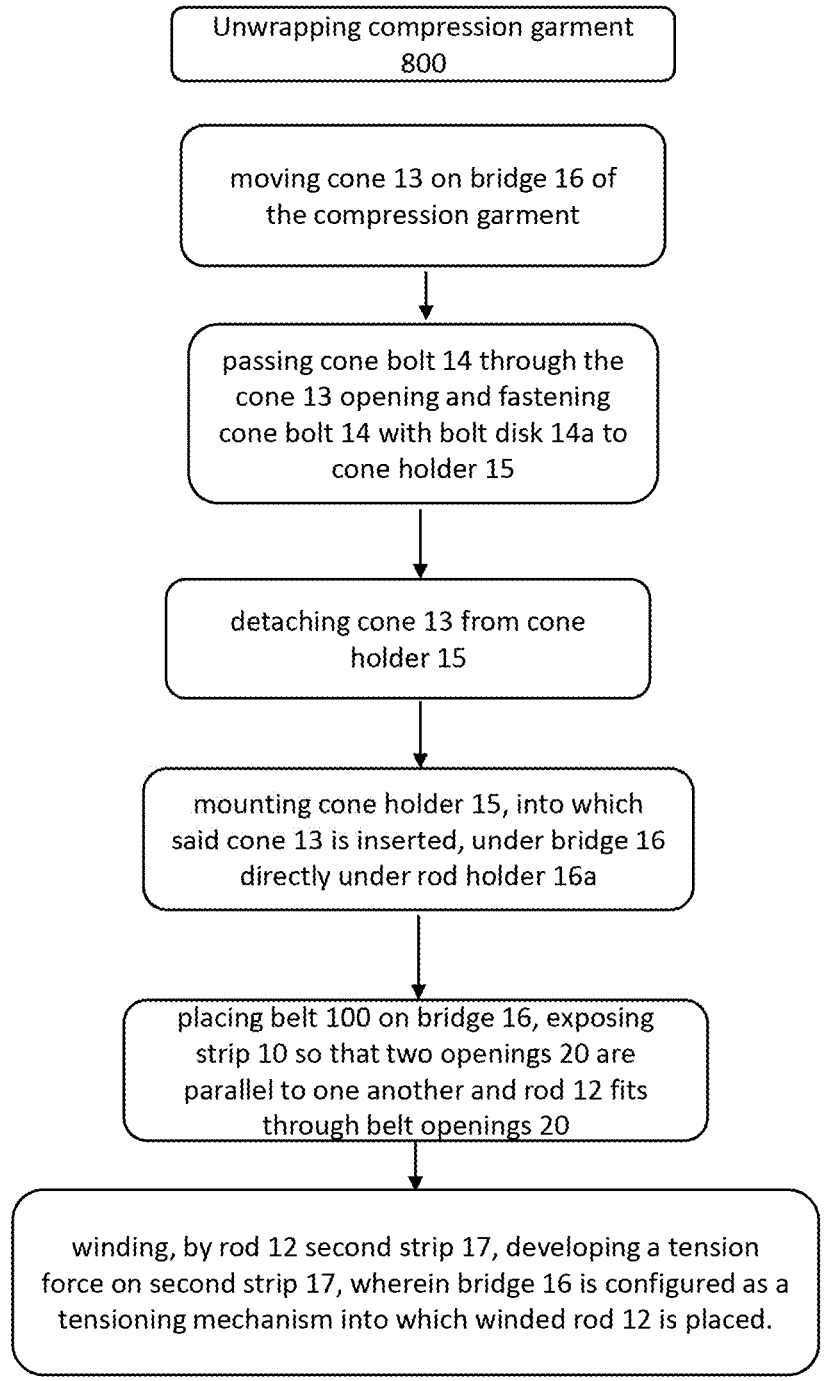
FIG. 35 is a flowchart of one embodiment of the method.
Figure 36:
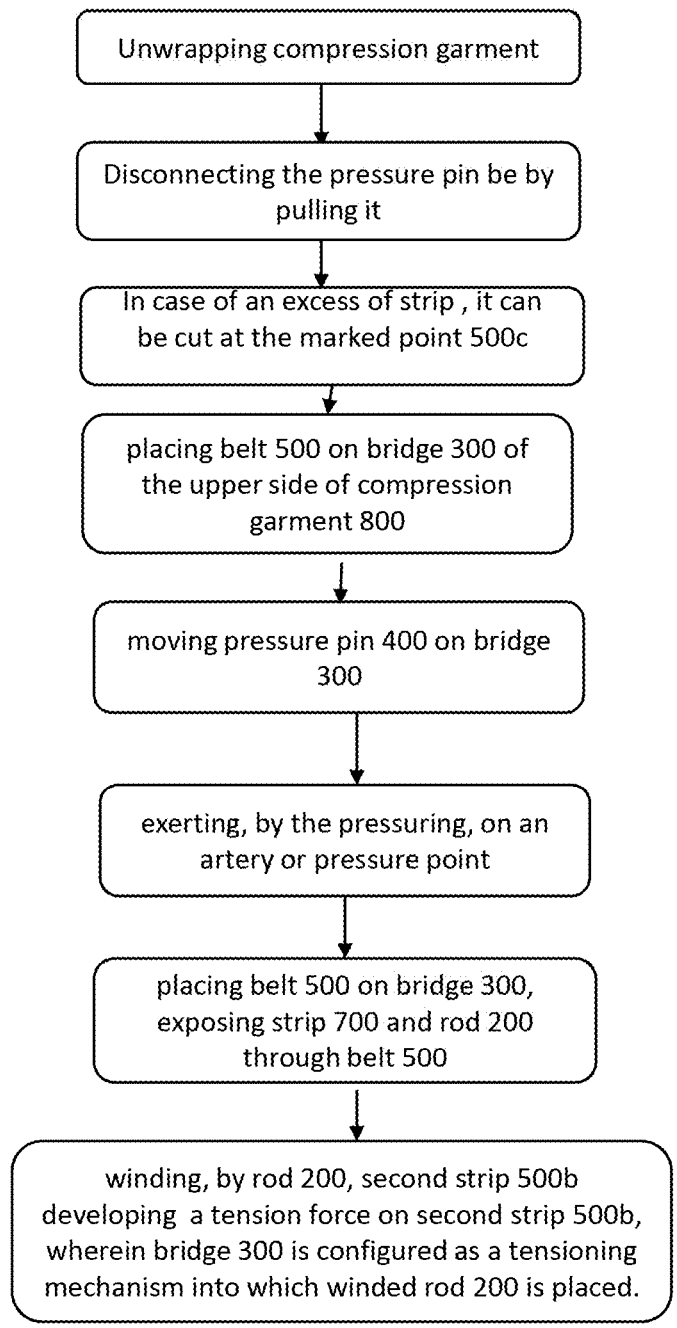
FIG. 36 is a flowchart of another embodiment of the method.

In exemplary embodiments, rod 200 winds strip 500b so as to develop a tension force on inner strip 500b. When the needed tension by winding strip 500b is achieved, rod 200 is placed through rod secure strip 700 as shown in FIG. 34.

In exemplary embodiments, bridge 300 acts as a tensioning mechanism, into which the winding rod 200 is placed so as to maintain the tension after rod 200 winds strip 500b.

Figure 27:
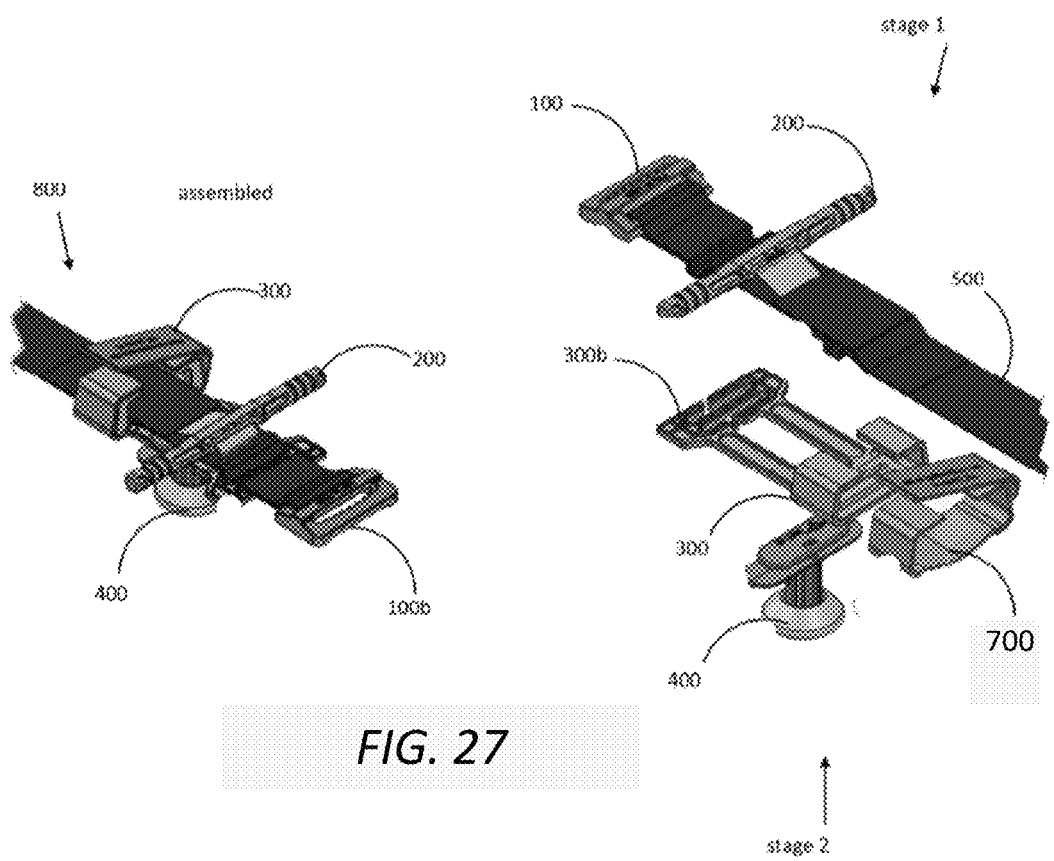
FIG. 27 is an illustration of an exemplary embodiment of the assembling steps of the compression garment, in accordance with some embodiments of the disclosure.
Figure 28:
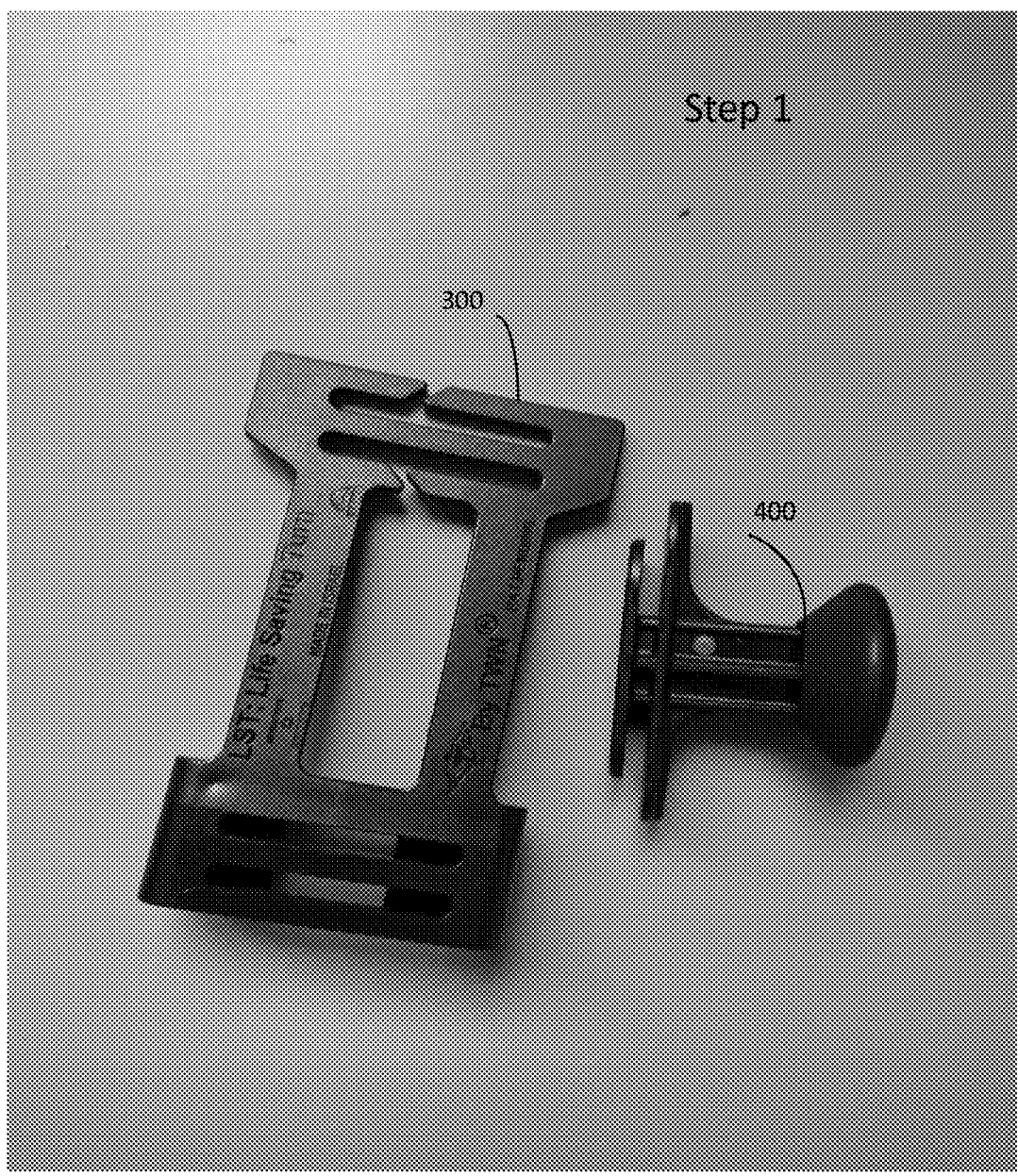
FIG. 28 is a picture of the rode secure strip and the pressure pin showing step 1 of the assembling method.
Figure 29:
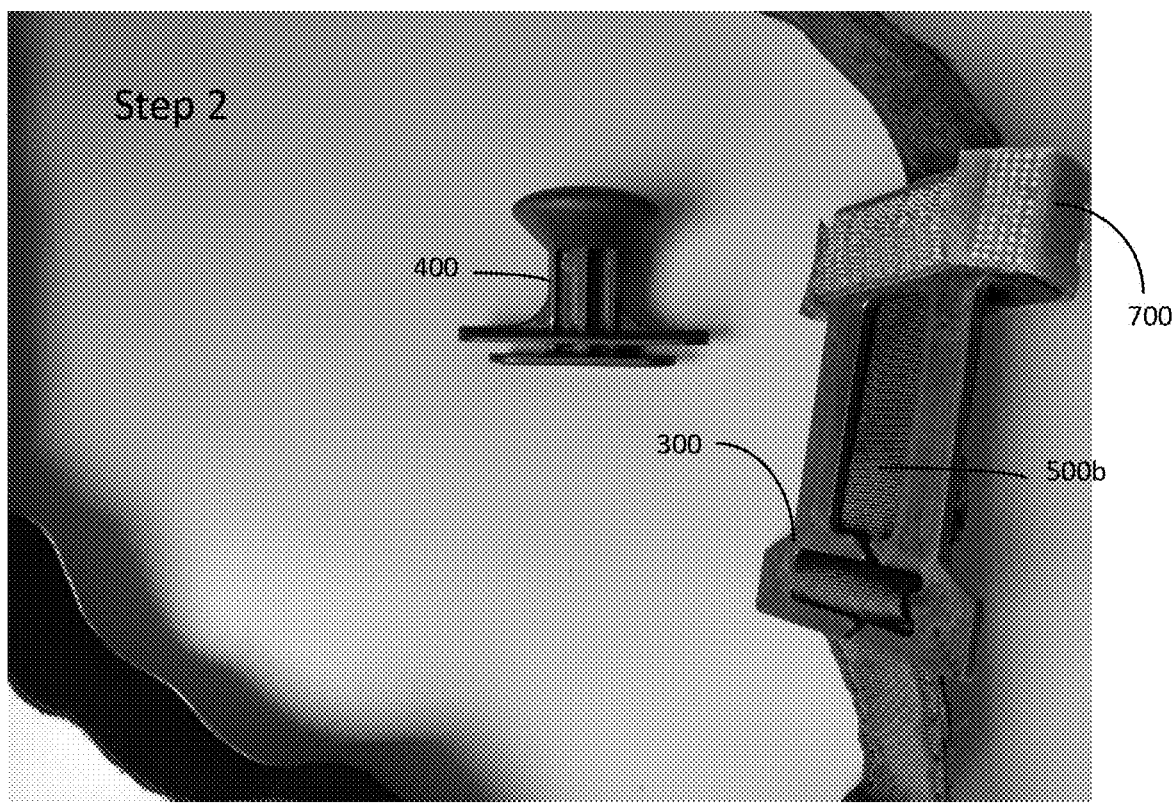
FIG. 29 is a picture of the rode secure strip and the pressure pin showing step 2 of the assembling method.
Figure 30:
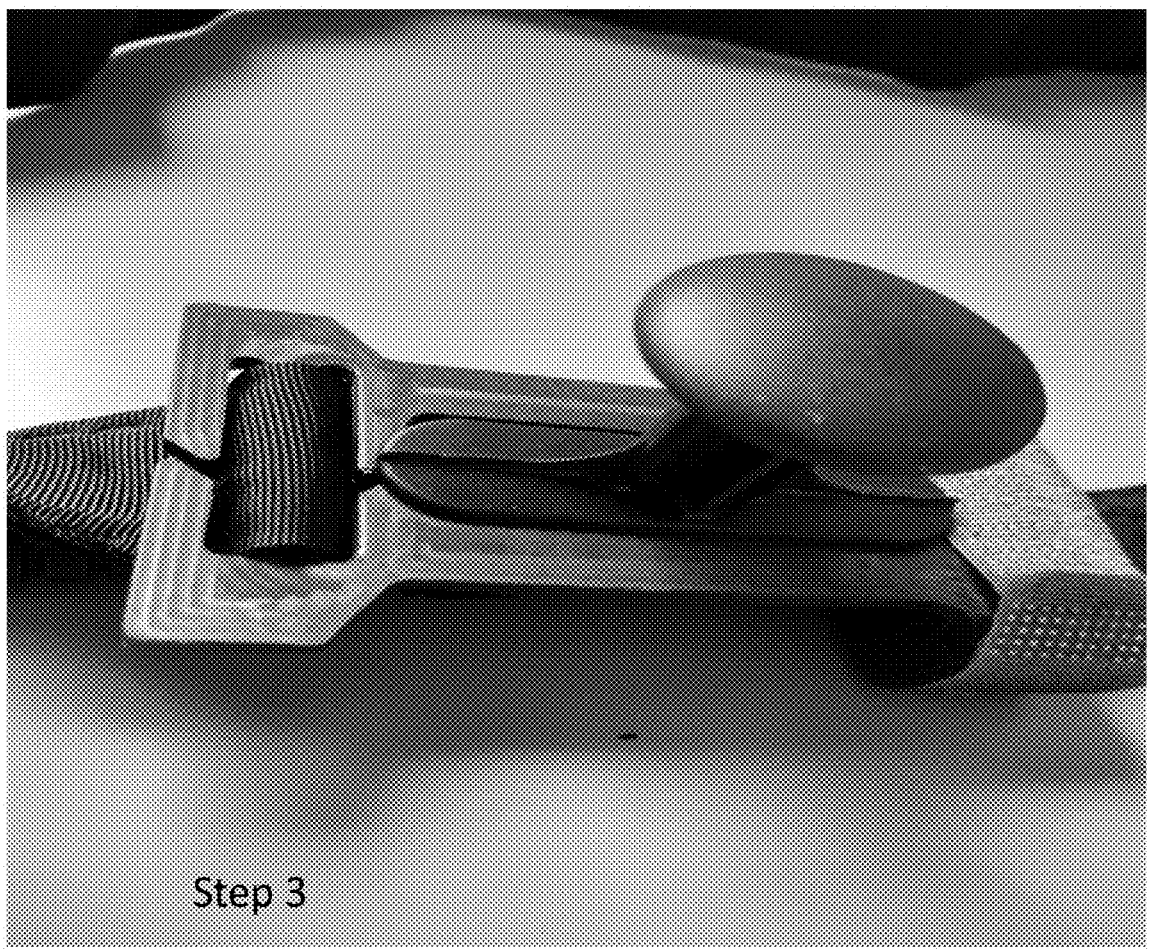
FIG. 30 is a picture of the rode secure strip and the pressure pin showing step 3 of the assembling method.
Figure 31:
FIG. 31 is a picture of the rode secure strip and the pressure pin showing step 4 of the assembling method.
Figure 32:
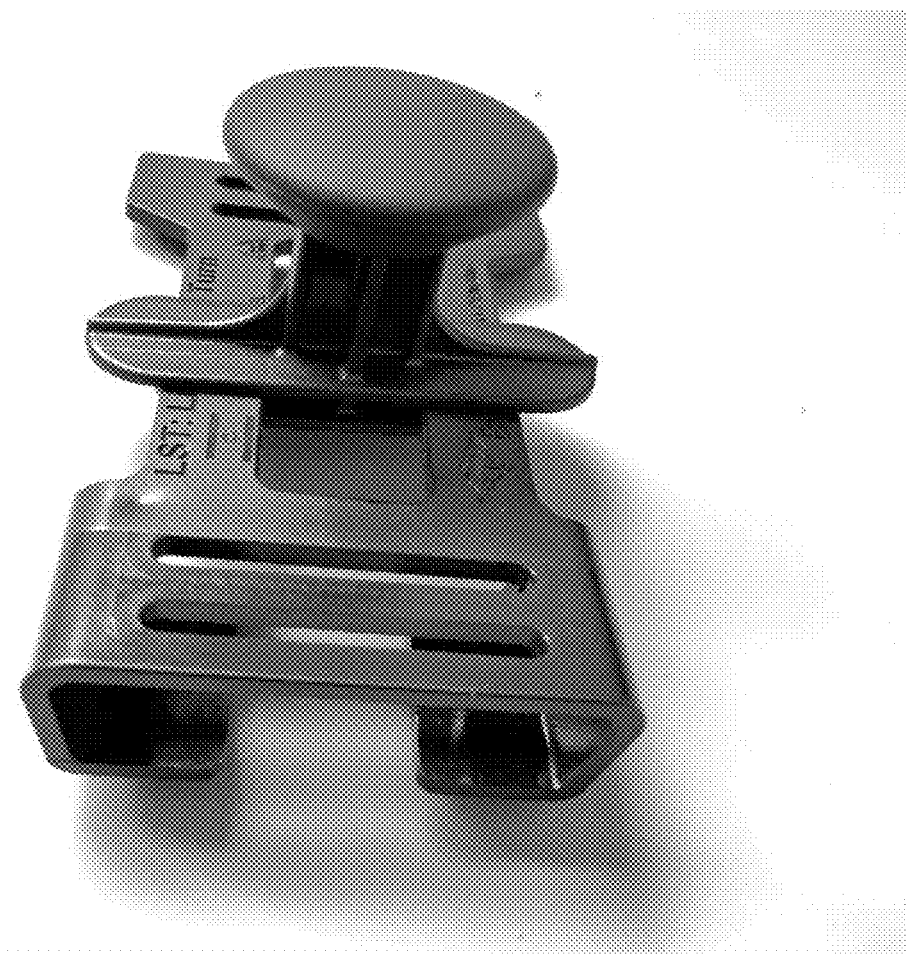
FIG. 32 is a picture of the rode secure strip and the pressure pin showing step 5 of the assembling method.

As shown in FIG. 27, in exemplary embodiments, rod secure strip 700, into which pressure pin 400 is inserted, is mounted under bridge 300 and directly under rod secure strip 700, in such a way that pressure pin 400 is located in the center of the bridge 300.

Tourniquets should generally remain inflated maximal time of 1.5 to 2 hours, the time in which most wounded people can get to a hospital. Therefore, having a garment in place for two or fewer hours should not have any ill effects beyond those caused by the injury requiring the tourniquet. A garment that continues to restrict blood flow often leads to deep vein thrombosis (DVT), a dangerous and life-threatening complication that can cause permanent injury, even death. Therefore, there is a special place on rod secure strip 700 to note the time.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

It is to be fully understood that certain aspects, characteristics, and features, of the disclosure, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the disclosure which are illustratively described and presented in combination or sub-combination in the context or format of a single embodiment, may also be illustratively described and presented in the context or format of a plurality of separate embodiments.

Although the disclosure has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, are encompassed by the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present disclosure. To the extent that section headings are used, they should not be construed as necessarily limiting.

What is claimed is:

1. A compression garment for winding and applying a tension force, comprising:
    a belt comprising a first strip having two belt openings and a second strip being a smooth fabric;
    a buckle;
    a rod and a rod holder configured for holding said rod wherein said second strip is threaded into said rod, folded in half and enters said first strip along with said rod;
    a compression unit comprising a cone, a cone bolt, a bolt disk, a cone holder having a cone holder opening for said cone bolt attaching said cone to said cone holder, and a bridge configured on upper side of said belt openings;
    wherein said cone has a cone opening through which said cone bolt may enter and be screwed with said bolt disk to said cone holder;
    wherein said cone is moveable on said bridge, and is configured detached from said cone holder, or connected to said cone holder via said bolt disk screwed to said cone bolt passing through said cone opening, and said cone is configured to exert pressure on an artery or pressure point;
    wherein said cone holder, into which said cone is inserted, is mounted under said bridge directly under said rod holder;
    wherein said belt is configured for being placed on said bridge, so as to expose said strip and said rod through said belt openings;
    wherein said rod winds said second strip, so as to develop a tension force on said second strip; and
    wherein said bridge is configured as a tensioning mechanism into which said winded rod is placed.

2. The garment of claim 1, wherein said cone is either detached or connected to said bridge, according to a type of injury or wound.

3. The garment of claim 1, wherein said cone is fixed so that it exerts pressure on a desired artery, on pressure points, without being fixed to said bridge, and only under said belt.

4. The garment of claim 3, wherein said cone automatically enters a correct place when applying pressure on a femoral artery leading to a leg or on a subclavian artery, leading to a shoulder area, even if an exact location of the artery is not identified.

5. The garment of claim 1, wherein said cone is placed on upper region of a pelvis, in case of injury to an upper thigh or amputation of a leg, or over a subclavian artery, in cases of arm amputation, or injury in a shoulder area.

6. The garment of claim 1, further comprising a clock mounted on a clock holder having a clock holder opening mounted on top of said rod holder.

7. The garment of claim 6, wherein said clock is a mechanical device configured not to move by itself, and to be set by a therapist or medical assistant.

8. The garment of claim 6, wherein said clock includes a hand configured for manually setting a time of initial application of the tourniquet.

9. The garment of claim 8, wherein position of said hand is in a 'no move' position on said clock when not used or when said clock is in a fixed position.

10. The garment of claim 8, wherein when said hand is in a 'raised' position, said hand can be moved, and when said hand is in a 'fixed' position, said hand does not move.

11. The garment of claim 8, wherein said hand is configured for making a sound every hour.

12. The garment of claim 8, wherein said hand is configured for vibrating when moving, whereby vibrations of said hand are noticeable.

13. A method of winding a compression garment, comprising:
- moving a cone of the compression garment on a bridge of the compression garment, the compression garment comprising a belt comprising a first strip having two belt openings, and a second strip being a smooth fabric, a buckle, a rod and a rod holder configured for holding said rod, and a compression unit comprising the cone, a cone bolt, a bolt disk, a cone holder having a cone holder opening for said cone bolt attaching said cone to said cone holder, and the bridge configured on upper side of said belt openings;
- passing the cone bolt through a cone opening and fastening the cone bolt with said bolt disk to said cone holder;
- detaching the cone from the cone holder;
- mounting said cone holder, into which said cone is inserted, under said bridge directly under said rod holder;
- placing said belt on said bridge, so as to expose said strip and said rod through said belt openings;
- winding, by said rod, said second strip, so as to develop a tension force on said second strip, wherein said bridge is configured as a tensioning mechanism into which said winded rod is placed.

14. The method of claim 13 wherein the through the opening of the cone the cone bolt may enter and be screwed with the bolt disk to the cone holder.

15. The method of claim 13 wherein the cone is dynamic (translatable, moveable) on and along the bridge.

16. The method of claim 13 wherein the cone is fixed and static at a selected location along the bridge.

17. The method of claim 13 wherein the cone can be either detached or connected, according to the injury and wound.

18. The method of claim 13 wherein the cone is fixed, so as to exert pressure on the desired artery without being fixed to the bridge, but only under the belt.

19. The method of claim 13 wherein in case of injury to the upper thigh or amputation of a leg, the cone is placed on the upper region of the pelvis.

20. A compression garment for winding and applying a tension force, comprising:
- a belt comprising a first strip being a scotch fabric and a second strip being a smooth fabric;
- a buckle;
- a bridge configured on upper side of said belt;
- a rod and a rod secure strip configured for holding said rod;
- wherein said second strip is threaded into said rod, folded in half and enters said first strip along with said rod;
- a compression unit comprising a pressure pin having a closing lever attaching said pressure pin to the bridge, wherein said pressure pin is moveable on said bridge, comprising two plastic plates or other hard material and in between the two plates is a gap, and said pressure pin is configured to exert pressure on an artery or pressure point;
- wherein said belt is configured for being placed on said bridge, so as to expose said strip and said rod through said belt;
- wherein said rod winds said second strip, so as to develop a tension force on said second strip; and
- wherein said bridge is configured as a tensioning mechanism into which said winded rod is placed.

* * * * *